United States Patent
Maki et al.

(10) Patent No.: US 10,814,038 B2
(45) Date of Patent: Oct. 27, 2020

(54) COMBINATION COMPOSITIONS

(71) Applicants: 3-D Matrix, Ltd., Tokyo (JP); Vicus Therapeutics, LLC, Morristown, NJ (US)

(72) Inventors: John Maki, Mendham, NJ (US); Eun Seok Gil, Acton, MA (US); Lisa Spirio, Lexington, MA (US)

(73) Assignees: 3-D Matrix, Ltd., Tokyo (JP); Vicus Therapeutics, LLC, Morristown, NJ (US)

( * ) Notice: Subject to any disclaimer, the term of this patent is extended or adjusted under 35 U.S.C. 154(b) by 0 days.

(21) Appl. No.: 16/064,180

(22) PCT Filed: Dec. 29, 2016

(86) PCT No.: PCT/US2016/069133
§ 371 (c)(1),
(2) Date: Jun. 20, 2018

(87) PCT Pub. No.: WO2017/120092
PCT Pub. Date: Jul. 13, 2017

(65) Prior Publication Data
US 2018/0369452 A1 Dec. 27, 2018

Related U.S. Application Data

(60) Provisional application No. 62/275,752, filed on Jan. 6, 2016.

(51) Int. Cl.
| | | |
|---|---|---|
| A61L 27/50 | (2006.01) |
| A61K 38/08 | (2019.01) |
| A61L 27/06 | (2006.01) |
| A61K 9/00 | (2006.01) |
| A61K 38/10 | (2006.01) |
| A61L 27/10 | (2006.01) |
| A61L 27/04 | (2006.01) |
| A61K 47/42 | (2017.01) |
| A61K 38/16 | (2006.01) |
| A61L 27/22 | (2006.01) |
| A61K 45/06 | (2006.01) |

(52) U.S. Cl.
CPC ............ *A61L 27/50* (2013.01); *A61K 9/0019* (2013.01); *A61K 38/08* (2013.01); *A61K 38/10* (2013.01); *A61K 38/16* (2013.01); *A61K 47/42* (2013.01); *A61L 27/047* (2013.01); *A61L 27/06* (2013.01); *A61L 27/10* (2013.01); *A61L 27/227* (2013.01); *A61K 45/06* (2013.01); *A61K 2300/00* (2013.01)

(58) Field of Classification Search
CPC ...... A61K 38/08; A61K 47/42; A61K 9/0019; A61K 38/10; A61K 38/16; A61K 2300/00; A61K 45/06; A61L 27/047; A61L 27/06; A61L 27/10; A61L 27/227; A61L 27/50
See application file for complete search history.

(56) References Cited

U.S. PATENT DOCUMENTS

| | | |
|---|---|---|
| 4,466,641 A | 8/1984 | Heilman et al. |
| 4,582,640 A | 4/1986 | Smestad et al. |
| 4,642,117 A | 2/1987 | Nguyen et al. |
| 4,947,840 A | 8/1990 | Yannas et al. |
| 5,110,604 A | 5/1992 | Chu et al. |
| 5,126,141 A | 6/1992 | Henry |
| 5,236,903 A | 8/1993 | Saiki et al. |
| 5,292,514 A | 3/1994 | Capecchi et al. |
| 5,510,102 A | 4/1996 | Cochrum |
| 5,527,610 A | 6/1996 | Urry |
| 5,550,187 A | 8/1996 | Rhee et al. |
| 5,670,483 A | 9/1997 | Zhang et al. |
| 5,747,452 A | 5/1998 | Ruoslahti et al. |
| 5,773,577 A | 6/1998 | Cappello |
| 5,955,343 A | 9/1999 | Holmes et al. |
| 6,046,160 A | 4/2000 | Obi-Tabot |
| 6,224,893 B1 | 5/2001 | Langer et al. |
| 6,280,474 B1 | 8/2001 | Cassidy et al. |
| 6,548,630 B1 | 4/2003 | Zhang et al. |
| 6,730,298 B2 | 5/2004 | Griffith-Cima et al. |
| 6,800,481 B1 | 10/2004 | Holmes et al. |
| 7,098,028 B2 | 8/2006 | Holmes et al. |
| 7,449,180 B2 | 11/2008 | Kisiday et al. |
| 7,713,923 B2 | 5/2010 | Genove et al. |
| 7,846,891 B2 | 12/2010 | Ellis-Behnke et al. |
| 8,022,178 B2 | 9/2011 | Horii et al. |
| 9,012,404 B2 | 4/2015 | Spirio et al. |
| 9,084,837 B2 | 7/2015 | Ellis-Behnke et al. |

(Continued)

FOREIGN PATENT DOCUMENTS

| | | |
|---|---|---|
| CA | 2572964 A1 | 2/2006 |
| CA | 2618184 A1 | 12/2006 |

(Continued)

OTHER PUBLICATIONS

Zhang et al. High shear mixers: A review of typical applications and studies on power draw, flow pattern, energy dissipation and transfer properties. Chemical Engineering and Processing. vols. 56-57, pp. 25-41. (Year: 2012).*
Gasiorowski et al. Directed Intermixing in Multicomponent Self-Assembling Biomaterials. Biomacromolecules. vol. 12, pp. 3549-3559. (Year: 2011).*
Gao. Self-assembly and Gelation Properties of Novel Peptides for Biomedical Applications. Accessed online at https://www.escholar.manchester.ac.uk/api/datastream?publicationPid=uk-ac-man-scw:200520&datastreamId=FULL-TEXT.PDF on Jan. 14, 2020. 180 pages. (Year: 2013).*
Guvendiren et al. Shear-thinning hydrogels for biomedical applications. Soft Matter, 2012, vol. 8, pp. 260-272. (Year: 2012).*

(Continued)

*Primary Examiner* — Marcela M Cordero Garcia
(74) *Attorney, Agent, or Firm* — IP Supra, PLLC; Constantine Linnik; Robert Kelley Roth

(57) ABSTRACT

Combination compositions comprising self-assembling peptides and payload agents, and methods of making and using such compositions, are described.

29 Claims, 13 Drawing Sheets
Specification includes a Sequence Listing.

(56) References Cited

U.S. PATENT DOCUMENTS

| | | | |
|---|---|---|---|
| 9,162,005 B2 | 10/2015 | Ellis-Behnke et al. | |
| 9,327,010 B2 | 5/2016 | Ellis-Behnke et al. | |
| 9,339,476 B2 | 5/2016 | Norchi et al. | |
| 9,364,513 B2 | 6/2016 | Ellis-Behnke et al. | |
| 9,415,084 B2 | 8/2016 | Ellis-Behnke et al. | |
| 9,439,941 B2 | 9/2016 | Ellis-Behnke et al. | |
| 9,724,448 B2 | 8/2017 | Kobayashi et al. | |
| 10,245,299 B2 | 4/2019 | Mehta et al. | |
| 10,369,237 B2* | 8/2019 | Gil | A61L 2/04 |
| 10,576,123 B2 | 3/2020 | Takamura et al. | |
| 10,654,893 B2* | 5/2020 | Gil | A61L 27/227 |
| 2002/0160471 A1 | 10/2002 | Kisiday et al. | |
| 2003/0069177 A1 | 4/2003 | Dubaquie et al. | |
| 2003/0166846 A1 | 9/2003 | Rothstein et al. | |
| 2004/0204561 A1 | 10/2004 | Ellison | |
| 2004/0242469 A1 | 12/2004 | Lee et al. | |
| 2005/0181973 A1 | 8/2005 | Genove et al. | |
| 2005/0287186 A1 | 12/2005 | Ellis-Behnke et al. | |
| 2006/0084607 A1 | 4/2006 | Spirio et al. | |
| 2006/0111408 A1 | 5/2006 | Barlaam et al. | |
| 2006/0148703 A1 | 7/2006 | Lee et al. | |
| 2006/0293243 A1 | 12/2006 | Puri et al. | |
| 2007/0128175 A1 | 6/2007 | Ozbas et al. | |
| 2007/0190603 A1 | 8/2007 | Holmes et al. | |
| 2008/0032934 A1 | 2/2008 | Ellis-Behnke et al. | |
| 2008/0091233 A1 | 4/2008 | Ellis-Behnke et al. | |
| 2009/0053103 A1 | 2/2009 | Mortimer et al. | |
| 2009/0054405 A1 | 2/2009 | Booker et al. | |
| 2009/0111734 A1 | 4/2009 | Ellis-Behnke et al. | |
| 2009/0162437 A1* | 6/2009 | Horii | A61L 27/227 424/484 |
| 2009/0169598 A1 | 7/2009 | Crutcher | |
| 2010/0143504 A1 | 6/2010 | Spirio et al. | |
| 2010/0311640 A1 | 12/2010 | Genove et al. | |
| 2011/0002880 A1 | 1/2011 | Takamura et al. | |
| 2011/0201541 A1 | 8/2011 | Takamura et al. | |
| 2012/0010140 A1 | 1/2012 | Ellis-Behnke et al. | |
| 2012/0058066 A1 | 3/2012 | Nagai et al. | |
| 2012/0070427 A1* | 3/2012 | Kaplan | A61K 9/0024 424/130.1 |
| 2013/0281547 A1 | 10/2013 | Spirio et al. | |
| 2013/0296239 A1 | 11/2013 | Takamura et al. | |
| 2014/0038909 A1 | 2/2014 | Takamura et al. | |
| 2014/0286888 A1 | 9/2014 | Nagai et al. | |
| 2014/0329914 A1 | 11/2014 | Kobayashi et al. | |
| 2015/0105336 A1 | 4/2015 | Takamura et al. | |
| 2015/0197359 A1 | 7/2015 | Nohara et al. | |
| 2015/0258166 A1 | 9/2015 | Spirio et al. | |
| 2015/0290329 A1* | 10/2015 | Heilshorn | A61K 9/0024 514/773 |
| 2015/0328279 A1 | 11/2015 | Ellis-Behnke et al. | |
| 2016/0000966 A1 | 1/2016 | Kobayashi et al. | |
| 2016/0015855 A1 | 1/2016 | Nohara et al. | |
| 2016/0030628 A1 | 2/2016 | Kobayashi | |
| 2016/0213906 A1 | 7/2016 | Horita et al. | |
| 2016/0287744 A1 | 10/2016 | Kobayashi et al. | |
| 2016/0317607 A1 | 11/2016 | Spirio et al. | |
| 2016/0362451 A1 | 12/2016 | Gil et al. | |
| 2017/0072008 A1 | 3/2017 | Mehta et al. | |
| 2017/0128622 A1 | 5/2017 | Spirio et al. | |
| 2017/0173105 A1 | 6/2017 | Mehta et al. | |
| 2017/0173221 A1 | 6/2017 | Mehta et al. | |
| 2017/0202986 A1 | 7/2017 | Gil et al. | |
| 2019/0111165 A1 | 4/2019 | Gil et al. | |

FOREIGN PATENT DOCUMENTS

| | | | |
|---|---|---|---|
| CN | 101198350 A | 6/2008 | |
| CN | 101378773 A | 3/2009 | |
| CN | 101514225 A | 8/2009 | |
| EP | 2146667 A2 | 1/2010 | |
| EP | 2345433 A1 | 7/2011 | |
| EP | 2823830 A1 | 1/2015 | |
| EP | 3031466 A1 | 6/2016 | |
| JP | 2005-515796 A | 6/2005 | |
| JP | 2005-263631 A | 9/2005 | |
| JP | 2007-105186 A | 4/2007 | |
| JP | 2007-526232 A | 9/2007 | |
| JP | 2008-505919 A | 2/2008 | |
| JP | 2008-539257 A | 11/2008 | |
| JP | 2008-546689 A | 12/2008 | |
| JP | 2009-011341 A | 1/2009 | |
| JP | 2009-535338 A | 10/2009 | |
| JP | 2010-280719 A | 12/2010 | |
| JP | 2012-082180 A | 4/2012 | |
| JP | 5255274 B2 | 8/2013 | |
| JP | 2014-527543 A | 10/2014 | |
| JP | 5730828 B2 | 6/2015 | |
| JP | 5922749 B2 | 5/2016 | |
| WO | WO-94/17811 A1 | 8/1994 | |
| WO | WO-1996/040033 A1 | 12/1996 | |
| WO | WO-1997/037694 A1 | 10/1997 | |
| WO | WO-99/53019 A1 | 10/1999 | |
| WO | WO-00/01238 A1 | 1/2000 | |
| WO | WO-2002/022072 A2 | 3/2002 | |
| WO | WO-02/062969 A2 | 8/2002 | |
| WO | WO-2002/058749 A2 | 8/2002 | |
| WO | WO-2002/062961 A2 | 8/2002 | |
| WO | WO-03/084980 A2 | 10/2003 | |
| WO | WO-03/096972 A2 | 11/2003 | |
| WO | WO-2004/007532 A2 | 1/2004 | |
| WO | WO-2005/001076 A2 | 1/2005 | |
| WO | WO-2005/014615 A2 | 2/2005 | |
| WO | WO-2005/082399 A2 | 9/2005 | |
| WO | WO-2006/014570 A2 | 2/2006 | |
| WO | WO-2006/116524 A1 | 11/2006 | |
| WO | WO-2006/138023 A1 | 12/2006 | |
| WO | WO-2007/076032 A2 | 7/2007 | |
| WO | WO-2007/142757 A2 | 12/2007 | |
| WO | WO-2008/039483 A2 | 4/2008 | |
| WO | WO-2008/073392 A2 | 6/2008 | |
| WO | WO-2008/073395 A2 | 6/2008 | |
| WO | WO-2008/113030 A2 | 9/2008 | |
| WO | WO-2008/127607 A2 | 10/2008 | |
| WO | WO-2008/134544 A1 | 11/2008 | |
| WO | WO-2009/072556 A1 | 6/2009 | |
| WO | WO2010017469 * | 2/2010 | B25C 1/06 |
| WO | WO 2010017469 | 2/2010 | |
| WO | WO-2010/041636 A1 | 4/2010 | |
| WO | WO 2010/147763 | 12/2010 | |
| WO | WO2010147763 * | 12/2010 | A61M 1/34 |
| WO | WO-2012/008967 A1 | 1/2012 | |
| WO | WO-2013/030673 A2 | 3/2013 | |
| WO | WO2014017913 | 5/2013 | |
| WO | WO-2013/133413 A1 | 9/2013 | |
| WO | WO-2014/008400 A2 | 1/2014 | |
| WO | WO2014017913 * | 1/2014 | C08B 37/14 |
| WO | WO-2014/076660 A1 | 5/2014 | |
| WO | WO-2014/136081 A1 | 9/2014 | |
| WO | WO-2014/141143 A1 | 9/2014 | |
| WO | WO-2014/141160 A1 | 9/2014 | |
| WO | WO-2015/027203 A1 | 2/2015 | |
| WO | WO-2015/030063 A1 | 3/2015 | |
| WO | WO-2015/136370 A2 | 9/2015 | |
| WO | WO-2015/138473 A1 | 9/2015 | |
| WO | WO-2015/138475 A1 | 9/2015 | |
| WO | WO-2015/138478 A1 | 9/2015 | |
| WO | WO-2015/138514 A1 | 9/2015 | |
| WO | WO-2017/120092 A1 | 7/2017 | |

OTHER PUBLICATIONS

Zhang et al. High shear mixers: A review of typical applications and studies on power draw, flow pattern, energy dissipation and transfer properties. Chemical Engineering and Processing, vol. 57-58, pp. 25-41 (Year: 2012).*

Aguado et al. Improving Viability of Stem Cells During Syringe Needle Flow Through the Design of Hydrogel Cell Carriers. Tissue Eng Part A., 18(7-8): 806-815. (Year: 2012).*

Anderson et al. Modulating the Gelation Properties of Self-Assembling Peptide Amphiphiles . ACS Nano. Nov. 24, 2009; 3(11): 3447-3454.. (Year: 2009).*

(56) References Cited

OTHER PUBLICATIONS

Introduction to Rheology, http://weitzlab.seas.harvard.edu/files/weitzlab/files/introductiontorheology2.pdf accessed online on Jan. 22, 2020, 31 pages (Year: 2020) (Year: 2020).*

Deshpande. Techniques in oscillatory shear rheology. SERC School-cum-Symposium on Rheology of Complex Fluids Jan. 4-9, 2010, Indian Institute of Technology Madras, Chennai, India https://physics.iitm.ac.in/~compflu/Lect-notes/abhijit.pdf, accessed online on Jan. 23, 2020, 23 pages. (Year: 2010).*

3-D Matrix Japan, Ltd. Company Profile Power Point, 32 pages, May 2005 (with English translation).

3-D Matrix Japan, Ltd., Products and FAQs, with English Translation, 14 pages. URL: http:/web.archive.org [Retrieved Oct. 21, 2016].

3D Matrix Japan, Company, Technology, Products, Technology, FAQs, Publication, Company, News, Contact, no English translation, 17 pages. URL: http://www.3d-matrix.co.jp/cm02.html [Retrieved Feb. 25, 2005].

3D Matrix Japan, Product Features, with English translation, 2 pages. URL: http://web.archive.org/web/20050416044014/http://www.3d-matrix.eo.jp/pr03.html [Retrieved Feb. 20, 2013].

3D Matrix Japan, Product List, with English translation, 2 pages. URL: http://web.archive.org/web/20050416043834/http://www.3d-matrix.co.jp/pr02.html [Retrieved Aug. 1, 2013].

3D Matrix Japan, Products, with English translation, 2 pages. URL: http://web.archive.org/web/20050415004502/http://www.3d-matrix.eo.jp/pr0I.html [Retreived Feb. 20, 2013].

3D-Matrix Japan, Products, FAQs, 8 pages, dispatched Sep. 20, 2011 [English translation].

Abukawa, H. et al, Reconstructing Mandibular Defects Using Autologous Tissue-Engineered Tooth and Bone Constructs, J. Oral Maxillofac. Surg., 67(2):335-347 (2009).

Allen, P. et al, Type I collagen, fibrin and PuraMatrix matrices provide permissive environments for human endothelial and mesenchymal progenitor cells to form neovascular networks, J. Tissue Eng. Regen Med., 5(4):e74-86 (2011).

Altman, M. et al., Conformational behavior of ionic self-complementary peptides, Protein Sci., 9(6):1095-105 (2000).

Anderson, I. The properties of hyaluronan and its role in wound healing, Prof. Nurse., 17(4):232-5 (2001).

BD PuraMatrix Peptide Hydrogel, Catalog No. 354250, BD Biosciences, 1-16 (2004).

BD PuraMatrix Peptide Hydrogel, Product Specification Sheet, 1 page.

Bouten, C.V. et al, Substrates for cardiovascular tissue engineering, Adv. Drug Deliv. Rev., 63(4-5):221-41 (2011).

Branco, M.C. and Schneider, J.P., Self-assembling materials for therapeutic delivery, Acta. Biomaterialia, 5(3): 817-831 (2009).

Caplan, M.R. et al., Control of self-assembling oligopeptide matrix formation through systematic variation of amino acid sequence, Biomaterials, 23(1):219-27 (2002).

Caplan, M.R. et al., Self-assembly of a beta-sheet protein governed by relief of electrostatic repulsion relative to van der Waals attraction, Biomacromolecules, 1(4):627-31 (2000).

Censi, R. et al, Hydrogels for protein delivery in tissue engineering, J. Control Release, 161(2):680-692 (2012).

Chen, K. et al, A Hybrid Silk/Rada-Based Fibrous Scaffold with Triple Hierarchy for Ligament Regeneration, Tissue Eng. Part A., 18(13-14):1399-409 (2012).

Chen, P., Self-assembly of ionic-complementary peptides: a physicochemical viewpoint, Colloids and Surfaces A: Physicochemical and Engineering Aspects, 261(1-3): 3-24 (2005).

Cigognini, D. et al, Evaluation of early and late effects into the acute spinal cord injury of an injectable functionalized self-assembling scaffold, PLoS One., 6(5): e19782 (2011).

Concaro, S. et al, Effect of different materials on the proliferation and migration of articular chondrocytes, Osteoarthritis and Cartilage, 15:Supplement B, pp. B119 (2007).

Cooper et al., "Testing the "critical-size" in calvarial bone defects: revisiting the concept of a critical-sized defect (CSD)," Plast Reconstr Surg. 125(6): 1685-1692, 2010.

Cunha, C. et al, Emerging nanotechnology approaches in tissue engineering for peripheral nerve regeneration, Nanomedicine, 7(1):50-59 (2011).

Curley, J.L. et al, Fabrication of micropatterned hydrogels for neural culture systems using dynamic mask projection photolithography, J. Vis. Exp., 48: 2636 (2011).

Davis, M.E. et al, Custom design of the cardiac microenvironment with biomaterials, Circ Res., 97(1):8-15 (2005).

Davis, M.E. et al, Local myocardial insulin-like growth factor 1 (IGF-1) delivery with biotinylated peptide nanofibers improves cell therapy for myocardial infarction, Proc. Natl. Acad. Sci. USA. ,103(21):8155-8160 (2006).

Davis, M.E. et al., Injectable self-assembling peptide nanofibers create intramyocardial microenvironments for endothelial cells, Circulation, 111(4):442-50 (2005).

Declaration of Dr. Terence Norchi, MD, for use in proceedings against EP 1879606, 4 pages (Mar. 31, 2016).

Declaration of Rutledge Ellis-Behnke for WO 2006/116524, 6 pages, Aug. 10, 2015.

Dutta, R.C. and Dutta, A.K., Comprehension of ECM-Cell dynamics: A prerequisite for tissue regeneration, Biotechnol. Adv., 28(6):764-769 (2010).

Dégano, I.R. et al, The effect of self-assembling peptide nanofiber scaffolds on mouse embryonic fibroblast implantation and proliferation, Biomaterials, 30(6):1156-65 (2009).

Eisenbud, D. et al, Hydrogel Wound Dressings: Where Do We Stand in 2003?, Ostomy Wound Manage, 49(10): 52-57 (2003).

Ellis-Behnke, R. et al, Crystal clear surgery with self-assembling molecules that act as a barrier in the brain and intestine, Abstracts/ Nanomedicine: Nanotechnology, Biology, and Medicine, 1:269-270 (2005).

Ellis-Behnke, R., At the nanoscale: nanohemostat, a new class of hemostatic agent, WIREs Nanomedicine and Nanobiotechnology, 3: 70-78 (2011).

Ellis-Behnke, R.G. et al, Nano neuro knitting: peptide nanofiber scaffold for brain repair and axon regeneration with functional return of vision, Proc. Natl. Acad. Sci. USA, 103(13):5054-5059 (2006).

Ellis-Behnke, R.G. et al., Nano hemostat solution: immediate hemostasis at the nanoscale, Nanomedicine, 2(4):207-15 (2006).

Experimental Report conducted at Arch Therapeutics, $(EAKA)_4$ Acetate, 6 pages, (Jul. 2014).

Experimental Report conducted by Ellis-Behnke, 1. Kidneys (rats), received May 12, 2017.

Garreta, E. et al, Osteogenic differentiation of mouse embryonic stem cells and mouse embryonic fibroblasts in a three-dimensional self-assembling peptide scaffold, Tissue Eng., 12(8):2215-27 (2006).

Gelain, F. et al., Designer self-assembling peptide scaffolds for 3-d tissue cell cultures and regenerative medicine, Macromol. Biosci., 7(5):544-51 (2007).

Gelain, F. et al., Slow and sustained release of active cytokines from self-assembling peptide scaffolds, Journal of Controlled Release, 145:231-239 (2010).

Gervaso, F. et al, The biomaterialist's task: scaffold biomaterials and fabrication technologies, Joints 1(3): 130-137 (2013).

Girt, S. and Bader, A., Improved preclinical safety assessment using micro-BAL devices: the potential impact on human discovery and drug attrition, Drug Discov. Today, 16(9-10):382-397 (2011).

Gonzales, A.L. et al., Integrin interactions with immobilized peptides in polyethylene glycol diacrylate hydrogels, Tissue Eng., 10(11-12):1775-86 (2004).

Guo, H.D. et al, Sustained delivery of VEGF from designer self-assembling peptides improves cardiac function after myocardial infarction, Biochem. Biophys. Res. Commun., 424(1):105-111 (2012).

Guo, H.D. et al, Transplantation of marrow-derived cardiac stem cells carried in designer self-assembling peptide nanofibers improves cardiac function after myocardial infarction, Biochem. Biophys. Res. Commun., 399(1):42-48 (2010).

Guo, J. et al, Reknitting the injured spinal cord by self-assembling peptide nanofiber scaffold, Nanomedicine, 3(4):311-321 (2007).

(56) References Cited

OTHER PUBLICATIONS

Gurski, L.A. et al, 3D Matrices for Anti-Cancer Drug Testing and Development, Oncology, Issues Jan./Feb. 2010: 20-25.
Hartgerink, J.D. et al., Peptide-amphiphile nanofibers: a versatile scaffold for the preparation of self-assembling materials, Proc. Natl. Acad. Sci. U S A., 99(8):5133-8 (2002).
Hemmrich, K. et al., Implantation of preadipocyte-loaded hyaluronic acid-based scaffolds into nude mice to evaluate potential for soft tissue engineering, Biomaterials, 26(34):7025-37 (2005).
Henriksson, H. et al, Investigation of different cell types and gel carriers for cell-based intervertebral disc therapy, in vitro and in vivo studies, J. Tissue Eng. Regen. Med., doi: 10.1002/term.480 (2011).
Henriksson, H.B. et al, Transplantation of human mesenchymal stems cells into intervertebral discs in a senogeneic porcine model, Spine (Phila Pa 1976), 34(2):141-148 (2009).
Hilton, J. R. et al, Wound Dressings in Diabetic Foot Disease, Clinical Infectious Diseases, 39: S100-3 (2004).
Hollinger, J.O. and Kleinschmidt, J.C., "The critical size defect as an experimental model to test bone repair materials," J. Craniofac Surg 1990(1): 60-68.
Holmes, T.C. et al., Extensive neurite outgrowth and active synapse formation on self-assembling peptide scaffolds, Proc. Natl. Acad. Sci. U S A., 97(12):6728-33 (2000).
Horii, A. et al, Biological designer self-assembling peptide nanofiber scaffolds significantly enhance osteoblast proliferation, differentiation and 3-D migration, PLoS One, 2(2):e190 (2007).
Hsieh, P.C. et al, Controlled delivery of PDGF-BB for myocardial protection using injectable self-assembling peptide nanofibers, J. Clin. Invest.,116(1):237-248 (2006).
Hsieh, P.C.H. et al, Local controlled intramyocardial delivery of platelet-derived growth factor improves postinfarction ventricular function without pulmonary toxicity, Circulation, 114(7):637-644 (2006).
Huang, A.H. et al, Mechanics and mechanobiology of mesenchymal stem cell-based engineered cartilage, J. Biomech., 43(1):128-136 (2010).
International Search Report of PCT/US2016/069133, 6 pages, dated Apr. 7, 2017.
Kates, Declaration of Steven Kates, Ph.D., Re: Japanese Patent Application No. 2008-509090 ("Third Party Declaration") (2012).
Kim, J.H. et al, The enhancement of mature vessel formation and cardiac function in infarcted hearts using dual growth factor delivery with self-assembling peptides, Biomaterials, 32(26):6080-6088 (2011).
Kisiday, J. et al., Self-assembling peptide hydrogel fosters chondrocyte extracellular matrix production and cell division: implications for cartilage tissue repair, Proc. Natl. Acad. Sci. U S A, 99(15):9996-10001 (2002).
Kohgo, T. et al, Poster 110: Bone Regeneration for Dental Implants Using Tissue-Engineered Bone With Self-Assembling Peptide Nanofiber 3-Dimensional (3D) Scaffolds, Journal of Oral and Maxillofacial Surgery, 65(9): Supplement, p. 43.e63 (2007).
Komatsu, S. et al, The Neutral Self-Assembling Peptide Hydrogel SPG-178 as a Topical Hemostatic Agent, PLoS One, 9(7): e102778 (2014).
Kopecek, J. and Yang, J., Peptide-directed self-assembly of hydrogels, Acta Biomaterialia, 5(3): 805-816 (2009).
Kumada, Y. and Zhang, S., Significant type I and type III collagen production from human periodontal ligament fibroblasts in 3D peptide scaffolds without extra growth factors, PLoS One, 5(4):e10305 (2010).
Kyle, S. et al., Production of self-assembling biomaterials for tissue engineering, Trends Biotechnol., 27(7):423-33 (2009).
Lampe, K.J. and Heilshorn, S.C., Building stem cell niches from the molecule up through engineered peptide materials, Neurosci. Lett., 519(2):138-46 (2012).
Leung, G.K. et al, Peptide nanofiber scaffold for brain tissue reconstruction, Methods Enzymol., 508:177-190 (2012).

Li, X. et al, Engineering neural stem cell fates with hydrogel design for central nervous system regeneration, Progress in Polymer Science, 37(8):1105-1129 (2012).
Liedmann, A. et al, Cultivation of human neural progenitor cells in a 3-dimensional self-assembling peptide hydrogel, J. Vis. Exp., (59):e3830 (2012).
Liu, J. et al., Controlled release of paclitaxel from a self-assembling peptide hydrogel formed in situ and antitumor study in vitro, International Journal of Nanomedicine, 6:2143-2153 (2011).
Liu, W-M. et al., Diversification of Microfluidic Chip for Applications in Cell-Based Bioanalysis, Chinese Journal of Analytical Chemistry, 40(1): 24-31 (2012).
Loo, Y. et al., From short peptides to nanofibers to macromolecular assemblies in biomedicine, Biotechnol. Adv., 30(3):593-603 (2012).
Luo, Z. et al, Fabrication of self-assembling d-form peptide nanofiber scaffold d-EAK16 for rapid hemostasis, Biomaterials, 32(8):2013-20 (2011).
Maher, S.A. et al, A nano-fibrous cell-seeded hydrogel promotes integration in a cartilage gap model, J. Tissue Eng. Regen. Med., 4(1):25-29 (2010).
Marston, W.A. et al., Initial report of the use of an injectable porcine collagen-derived matrix to stimulate healing of diabetic foot wounds in humans, Wound Repair Regen., 13(3):243-7 (2005).
Masuhara, H. et al, Novel infectious agent-free hemostatic material (TDM-621) in cardiovascular surgery, Ann. Thorac. Cardiovasc. Surg. Methods Enzymol., 18(5):444-451 (2012).
McGrath, A.M. et al, BD © PuraMatrix® peptide hydrogel seeded with Schwann cells for peripheral nerve regeneration, Brain Res. Bull., 83(5):207-213 (2010).
Meng, H. et al, Peripferal Nerve Regeneration in Response to Synthesized Nanofiber Scaffold Hydrogel, Life Science Journal, 9(1): 42-46 (2012).
Misawa, H. et al, PuraMatrix facilitates bone regeneration in bone defects of calvaria in mice, Cell Transplant, 15(10):903-910 (2006).
Mooney, M.P. and Siegel, M.I., Animal models for bone tissue engineering of critical-sized defects (CSDs), bone pathologies, and orthopedic disease states, In: Hollinger, JO.; Einhorn, TA.; Doll, BA.; Sfeir, C.,editors. Bone Tissue Engineering. Boca Raton, FL: C.R.C. Press, pp. 217-244 (2005).
Nakahara, H. et al, Bone repair using a hybrid scaffold of self-assembling peptide PuraMatrix and polyetheretherketone cage in rats, Cell T ansplant, 19(6):791-797 (2010).
Narmoneva, D.A. et al, Endothelial cells promote cardiac myocyte survival and spatial reorganization: implications for cardiac regeneration, Circulation, 110(8):962-968 (2004).
Narmoneva, D.A. et al., Self-assembling short oligopeptides and the promotion of angiogenesis, Biomaterials, 26(23):4837-46 (2005).
Nichol, J.W. et al, Co-culture induces alignment in engineered cardiac constructs via MMP-2 expression, Biochem. Biophys. Res. Commun., 373(3):360-365 (2008).
Nishimura, A. et al., Controlled release of insulin from self-assembling nanofiber hydrogel, PuraMatrix: application for the subcutaneous injection in rats, European Journal of Pharmaceutical Sciences, 45:1-7 (2012).
Ortinau, S. et al, Effect of 3D-scaffold formation on differentiation and survival in human neural progenitor cells, Biomed. Eng. Online, 9(1):70 (2010).
Osterman, D.G. and Kaiser, E.T., Design and characterization of peptides with amphiphilic beta-strand structures, J. Cell Biochem., 29(2):57-72 (1985).
Patterson, J. et al., Biomimetic materials in tissue engineering, Materialstoday, 13(1-2): 14-22 (2010).
Saiga, K. et al, Combined use of bFGF and GDF-5 enhances the healing of medial collateral ligament injury, Biochem. Biophys. Res. Commun., 402(2):329-334 (2010).
Sanborn, T.J. et al., A Thermally Triggered, Enzymatically Cross-linked PEG-Peptide Hydrogel for Biomaterial Applications, Presented at 2001 Annual Meeting, Americal Institute of Chemical Engineers, Reno, NV, Nov. 4-9, 2001.
Scalfani, A.P. and Romo, III., T., Injectable fillers for facial soft tissue enhancement, Facial Plast. Surg., 16(1):29-34 (2000).

(56) References Cited

OTHER PUBLICATIONS

Segers, V.F. and Lee, R.T., Local delivery of proteins and the use of self-assembling peptides, Drug Discov. Today, 12(13-14):561-8 (2007).

Segers, V.F.M. and Lee, R.T., Stem-cell therapy for cardiac disease, Nature 451, 937-942 (2008).

Segers, V.F.M. et al, Local delivery of protease-resistant stromal cell derived factor-1 for stem cell recruitment after myocardial infarction, Circulation, 116(15):1683-1692 (2007).

Semino, C.E. et al., Entrapment of migrating hippocampal neural cells in three-dimensional peptide nanofiber scaffold, Tissue Eng., 10(3-4):643-55 (2004).

Semino, C.E., Self-assembling peptides: from bio-inspired materials to bone regeneration, J. Dent Res., 87(7):606-616 (2008).

Serban, M.A. et al, Effects of extracellular matrix analogues on primary human fibroblast behavior, Acta Biomater., 4(1):67-75 (2008).

Shirai, K. et al, Multipotency of clonal cells derived from swine periodontal ligament and differential regulation by fibroblast growth factor and bone morphogenetic protein, J. Periodontal Res., 44(2):238-247 (2009).

Shivachar, A.C., Isolation and Culturing of Glial, Neuronal and Neural Stem Cell Types Encapsulated in Biodegradable Peptide Hydrogel, Topics in Tissue Engineering, vol. 4. Eds. N Ashammakhi, R Reis, & F Chiellini © 2008.

Song, H. et al, Hemostatic efficacy of biological self-assembling peptide nanofibers in a rat kidney model, Macromol Biosci., 10(1):33-39 (2010).

Spencer, N.J. et al, Peptide- and collagen-based hydrogel substrates for in vitro culture of chick cochleae, Biomaterials, 29(8):1028-1042 (2008).

Sur, S. et al, A hybrid nanofiber matrix to control the survival and maturation of brain neurons, Biomaterials, 33(2):545-55 (2012).

Takei, J., 3-Dimensional Cell Culture Scaffold for Everyone: Drug Screening, Tissue Engineering and Cancer Biology, AATEX, 11(3): 170-176 (2006).

Tam, J. et al., Fractional skin harvesting: autologous skin grafting without donor-site morbidity, Plastic and Reconstructive Surgery Global Open, 1(6): e47 (2013).

Thonhoff, J.R. et al, Compatibility of human fetal neural stem cells with hydrogel biomaterials in vitro, Brain Res., 1187:42-51 (2008).

Tokunaga, M. et al, Implantation of cardiac progenitor cells using self-assembling peptide improves cardiac function after myocardial infarction, J. Mol. Cell. Cardiol., 49(6):972-983 (2010).

Tokunou, T. et al, Engineering insulin-like growth factor-1 for local delivery, FASEB J., 22(6):1886-1893 (2008).

Tortora, G. J., Principles of Human Anatomy, Fifth Edition, Chapter 4: The Integumentary System, 98-100 (1989).

Uemura, M. et al, Matrigel supports survival and neuronal differentiation of grafted embryonic stem cell-derived neural precursor cells, J. Neurosci. Res., 88(3):542-551 (2010).

Van Putten, S.M. et al, The downmodulation of the foreign body reaction by cytomegalovirus encoded interleukin-10, Biomaterials, 30(5):730-735 (2008).

Wang, Q.G. et al, The composition of hydrogels for cartilage tissue engineering can influence glycosaminoglycan profile, Eur. Cell Mater, 19:86-95 (2010).

Wang. T. et al, Molecular Mechanisms of RAD16-1 Peptide on Fast Stop Bleeding in Rat Models, Int. J. Mol. Sci., 13: 15279-15290 (2012).

Written Opinion of PCT/US2016/069133, 8 pages, dated Apr. 7, 2017.

Wu, X. et al, Functional self-assembling peptide nanofiber hydrogel for peripheral nerve regeneration, Regenerative Biomaterials, 21-30 (2016).

Yamaoka, H. et al, Cartilage tissue engineering using human auricular chondrocytes embedded in different hydrogel materials, J. Biomed. Mater Res. A., 78(1):1-11 (2006).

Ye, Z. et al., Temperature and pH effects on biophysical and morphological properties of self-assembling peptide RADA16-I, J. Pept. Sci., 14(2):152-62 (2008).

Yla-Outinen, L. et al, Three-dimensional growth matrix for human embryonic stem cell-derived neuronal cells, J. Tissue Eng. Regen. Med., doi: 10.1002/term.1512 (2012).

Yoshimi, R. et al, Self-assembling peptide nanofiber scaffolds, platelet-rich plasma, and mesenchymal stem cells for injectable bone regeneration with tissue engineering, J. Craniofac. Surg., 20(5):1523-1530 (2009).

Yu, Y.C. et al., Construction of biologically active protein molecular architecture using self-assembling peptide-amphiphiles, Methods Enzymol., 289:571-87 (1997).

Zarzhitsky, S. and Rapaport, H., The interactions between doxorubicin and amphiphilic and acidic β-sheet peptides towards drug delivery hydrogels, J. Colloid Interface Sci. 360(2):525-531 (2011).

Zhang et al., Building from the Bottom Up, Materials Today, Review Feature, 20-27 (2003).

Zhang et al., Emerging Biological Materials Through Molecular Self-Assembly, Biotechnology Advances, 20: 321-339 (2002).

Zhang, S. et al, PuraMatrix: Self-Assembling Peptide Nanofiber Scaffolds, Scaffolding in Tissue Engineering, Chapter 15, 217-238 (1992).

Zhang, S. et al, Self-assembling peptides in biology, materials science and engineering, Peptide Science—Present and Future, 737-744 (1999).

Zhang, S. et al, Self-complementary oligopeptide matrices support mammalian cell attachment, Biomaterials, 16(18): 1385-1393 (1995).

Zhang, S., Hydrogels: Wet or let die, Nat. Mater., 3(1):7-8 (2004).

Zhao, X. et al., Recent development of peptide self-assembly, Progress in Natural Science.

Hsu, B. B. et al, Clotting Mimicry from Robust Hemostatic Bandages Based on Self-Assembling Peptides, ACS Nano, 9(9): 9394-9406 (2015).

Meng, H. et al, The effect of a self-assembling peptide nanofiber scaffold (peptide) when used as a wound dressing for the treatment of deep second degree burns in rats, J. Biomed. Mater Res. B. Appl. Biomater., 89(2): 379-91 (2009).

PuraStat® Synthetic Surgical Hemostatic Agent, Product Information, Nanotechnology Products Database, registration date Mar. 30, 2017, retrieved from <<https://product.statnano.com/product/8558>>, accessed on Oct. 11, 2019.

Taghavi, L, et al, Evaluation of the hemocompatability of RADA 16-1 peptide, J. Biomat. App.. 32(8): 1024-1031 (2018).

Xu, F. F. et al, Comparison between self-assembling peptide nanofiber scaffold (SAPNS) and fibrin sealant in neurosurgical hemostasis, Clin. Transl. Sci., 8(5): 490-4 (2015).

[No Author Listed] Fluid. Iwanami Rikagaku Dictionary, 3rd edition Incremental version, 2nd Print, Oct. 20, 1981, p. 1430, Partial English Translation, 1 Page.

Akers, M. J., Chapter 26: Parenteral Preparations, Remington: Essentials of Pharmaceutics, Edited by Linda Felton, Pharmaceutical Press, p. 497 (2012).

Arista™ Information Sheet, Medafor, Inc., 6 pages (2006).

Arosio, P. et al, End-to-end self-assembly of RADA 16-I nanofibrils in aqueous solutions, Biophys. J., 102(7): 1617-26 (2012).

Author Not Known, Medical Devices: Guidance Document, Borderline products, drug-delivery products and medical devices incorporating, as an integral part, an ancillary medicinal substance or an ancillary human blood derivative, European Commission, DG Enterprise and Industry, Directorate F, Unit F3 "Cosmetics and medical devices", 22 pages (Dec. 3, 2009) <http://ec.europa.eu/health/medical-devices/files/meddev/2_1_3_rev_3-12_2009_en.pdf> [last accessed on May 4, 2015].

Author Unknown, Acrodisc® Syringe Filter with Supor® Membrane -0.2 μm, 13mm (1000/pkg), Product ID: 4692, Pall Shop, accessed from <<https://shop.pall.com/us/en/laboratory/sterile-filtration-and-clarification/mycoplasma-reduction/acrodisc-syringe-filters-with-supor-membrane-zid4692>> (2019).

Author Unknown, AORNs Recommended Practices for Maintaining a Sterile Field is Up for Review and Public Comment Through Mar. 25, 2005, retrieved from <<https://www.infectioncontroltoday.

(56) References Cited

OTHER PUBLICATIONS com/guidelines/aorns-recommended-practices-maintaining-sterile-field-review-and-public-comment-through>>, accessed on Dec. 19, 2018 (23 pages).
Author Unknown, ISO 13485, Wikipedia, retrieved from <<https://en.wikipedia.org/w/index.php?title=IS0 13485&oldid=694123721>>. Accessed on Dec. 2, 2016.
Author Unknown, Medical Device, Wikipedia, retrieved from <<https://en.wikipedia.org/w/index.php?title=Medical_device&oldid=699710004>>, retrieved on Dec. 2, 2016.
Basford, P.J., et al., Endoscopic resection of sporadic duodenal adenomas: comparison of endoscopic mucosal resection (EMR) with hybrid endoscopic submucosal dissection (ESD) techniques and the risks of late delayed bleeding, Surg. Endosc., 28: 1594-1600 (2014).
Baumfalk and Finazzo, Filter Integrity testing helps to ensure that GMP sterility requirements are met, BioPharm International, 19(6): 1-3 (2006).
Beam, J., Wound Cleansing: Water or Saline?, Journal of Athletic Training, 41(2): 196-197 (2006).
Becton, Dickinson and Company, Positively Unique: BD PosiFlush™ Pre-Filled Syringes, Brochure, 6 pages (Jun. 2010).
Boyle, A. L., Applications of de novo designed peptides, Peptide Applications in Biomedicine, Biotechnology and Bioengineering, 51-86 (2017).
Cai, L. et al, Injectable Hydrogels with In Situ Double Network Formation Enhance Retention of Transplanted Stem Cells, Adv. Funct. Mater., 1-8 (2015).
Chambers, J. et al, Memorandum regarding Nucleic Acid and Peptide Claim Interpretation: "A" and "The," USPTO, 2 pages, Dec. 29, 2005.
CoSeal® Surgical Sealant, Information Sheet, Baxter Healthcare Corporation, 8 pages (2006).
Cryolife®, Life Restoring Technologies, BioGlue® Instructions for Use: Surgical Adhesive Syringe Instructions for Use, L6312.008— (Apr. 2014), pp. 1-15, 16 pages (2014).
Cunha, C. et al., 3D culture of adult mouse neural stem cells within functionalized self-assembling peptide scaffolds, International Journal of Nanomedicine, 943-955 (2011).
CyroLife: BioGlue® Surgical Adhesive, Products & Services, Website © 2007-2012,<http://web.archive.org/web/20120226221438/http://cryolife.com/products/bioglue-surgical-adhesive>, Retrieved Sep. 1, 2017.
Dojindo catalog, -SulfoBiotics- Sodium sulfide (Na2S), retrieved from http://www.dojindo.eu.com/store/p/885-SulfoBiotics-Sodium-sulfide-Na2S.aspx, 2 pages, downloaded Apr. 25, 2018.
Driscoll, P., What are the differences and similarities between laparoscopy and endoscopy?, 1 page (2016), <https//www.quora.com/what-are-the-differences-and-similiarities-between-laparoscopy-and-endoscopy> Retrieved on Oct. 4, 2017.
Gherli, T. et al., Comparing warfarin with aspirin after biological aortic valve replacement: a prospective study, Circulation, 110(5):496-500 (2004).
Ginsberg, M., Good Medicine/Bad Medicine and The Law of Evidence: Is There a Role for Proof of Character, Propensity, or Prior Bad Conduct in Medical Negligence Litigation?, South Caroline Law Review, 63:367-402 (2011).
Hielscher Ultrasound Technology, 2008, Ultrasonic Degassing and Defoaming of Liquids, accessed from https://www.hielscher.com/degassing_01.htm, on Mar. 27, 2019.
Hirai, K. et al, The fundamental study of Matrigel (PuraMatrix TM) for the hemostasis of bleeding from pulmonary artery and vein or the prevention of lung fistel, Gen Thorac Cardiovasc Surg, 59 (Supplement): 600 (2011).
Hwang, W. et al., Supramolecular structure of helical ribbons self-assembled from a beta-sheet peptide, The Journal of Chemical Physics, 118(1): 389-397 (2003).
Ingenito, E. P. et al, Bronchoscopic Lung Volume Reduction in Severe Emphysema, Proc. Am. Thorac. Soc., 5(4): 454-460 (2008).
InjectorForce Max™, Olympus, Brochure, 3 pages (2012).
Koh, R., et al. Antithrombotic drugs are risk factors for delayed postoperative bleeding after endoscopic submucosal dissection for gastric neoplasms, Gastrointest. Endosc., 78: 476-483 (2013).
Kubba, A.K. and Palmer, K. R., Role of endoscopic injection therapy in the treatment of bleeding peptic ulcer, British Journal of Surgery, 83: 461-468 (1996).
Kumada, Y. et al., Functionalized scaffolds of shorter self-assembling peptides containing MMP-2 cleavable motif promote fibroblast proliferation and significantly accelerate 3-D cell migration independent of scaffold stiffness, Soft Matter, The Royal Society of Chemistry, 7 pages (2010).
Kyle, S. et al, Recombinant self-assembling peptides as biomaterials for tissue engineering, Biomaterials, 31: 9395-9405 (2010).
Lao, W., Repair Medical Science and Tissue Engineering, Chemical Industry Press, 1st ed., pp. 91-93 (2003). [Chinese].
Lee, J. et al., Three-dimensional cell culture matrices: state of the art, Tissue Eng. Part B Rev., 14(1):61-86 (2008).
Leon, E.J. et al., Mechanical properties of a self-assembling oligopeptide matrix, J. Biomater. Sci. Polymer Edn., 9(3):297-312 (1998).
Lin, H.-J. et al, A prospective, randomized trial of large-versus small-volume endoscopic injection of epinephrine for peptic ulcer bleeding, Gastrointestinal Endoscopy, 55(6): 615-619 (2002).
Louie, M. K. et al, Bovine Serum Albumin Glutaraldehyde for Completely Sutureless Laparoscopic Heminephrectomy in a Survival Porcine Model, Journal of Endourology, 24(3): 451-455 (2010).
Luo, Z. and Zhang, S., Designer nanomaterials using chiral self-assembling peptide systems and their emerging benefit for society, Chem. Soc. Rev., 41(13):4736-54 (2012).
Lépilliez, V., et al., Endoscopic resection of sporadic duodenal adenomas: an efficient technique with a substantial risk of delayed bleeding, Endoscopy, 40: 806-810 (2008).
Marini, D.M. et al., Left-Handed Helical Ribbon Intermediates in the Self-Assembly of a beta-Sheet Peptide, Nano Letters, 2(4):295-299 (2002).
McFadden, P. M., Minimally Invasive Thoracic Surgery, vol. 2, No. 3, Jul. 2000, pp. 137-144.
Mimotopes, A Guide to Handling and Storing Peptides, PU3-004-1, Feb. 20, 2011, Date established via internet achieve http://www.mimotopes.com/files/editor_upload/File/PeptidesAndAntibodies/PU3004-1Handling-and-Storing-Peptides.PDF.
Moser, C. et al, Autologous fibrin sealant reduces the incidence of prolonged air leak and duration of the chest tube drainage after lung volume reduction surgery: a prospective randomized blinded study, Journal of Thoracic and Cardiovascular Surgery, 136(4): 843-849 (2008).
Olson, E. J., Hyperinflated Lungs: What does it mean?, a recent chest X-ray showed that I have hyperinflated lungs. What could cause this?, Mayo Clinic, Nov. 30, 2017, retrieved from <<https://www.mayoclinic.org/diseases-conditions/emphysema/expert-answers/hyperinflated-lungs/faq-20058169>>, 3 pages, accessed Feb. 14, 2019.
Ono, S. et al., Thienopyridine derivatives as risk factors for bleeding following high risk endoscopic treatments: Safe Treatment on Antiplatelets (STRAP) study, Endoscopy, 47: 632-637 (2015).
Paramasivam, E., Air leaks, pneumothorax, and chest drains, Continuing Education in Anesthesia, Critical Care & Pain, vol. 8 No. 6 2008.
Pioche, M. et al, a self-assembling matrix-forming gel can be easily and safely applied to prevent delayed bleeding after endoscopic resections, Endoscopy International Open, 4: E415-E419 (2016).
Reich, I. et al., Chapter 36: Tonicity, Osmoticity, Osmolality, and Osmolarity, Remington: Practice of The Science and Pharmacy, 19th edition, Mack Publishing Company, 613-621 (1995).
Sigma-Aldrich catalog, Sodium Bicarbonate, retrieved from https://www.sigmaaldrich.com/catalog/product/sigma/s5761 ?lang=en&region=US, 4 pages, downloaded on Apr. 25, 2018.
Spotnitz, W. D. and Banks, S., Hemostats, sealants and adhesives: components of the surgical toolbox, Transfusion, 48: 1502-1516 (2008).
Stark, J. and De Leval, M., Experience with fibrin seal (Tisseel) in operations for congenital heart defects, Ann. Thorac. Surg., 38(4):411-3 (1984).

(56) References Cited

OTHER PUBLICATIONS

Stiuso, P. et al., The self-association of protein SV-IV and its possible functional implications, Eur. J. Biochem., 266(3):1029-35 (1999).
Sun-Sri, TITAN2® 17mm filter, 2009, accessed from https://sun-sri.com/products/17mm_filters.aspx, accessed on May 22, 2019.
The University of Waterloo, Buffer Solutions, retrieved from https://web.archive.org/web/20001213162000/http://www.science.uwaterloo.ca/-cchieh/cact/c123/buffer.htm, 6 pages, downloaded on Apr. 24, 2018.
Thermo Scientific, MaxQ 2000 Open-Air Platform Shaker, 30 pages (2010).
Week 201413 Thomson Scientific, London, GB; AN 2013-U98585, XP0027 40500, Use of nigella glandulifera freyn 3 seed grass volatile oil for preparing medicine for treating chronic obstructive pulmonary disease, & CN 103 251 690 A People's Liberation Army Xinjiang Milita) Aug. 21, 2013 (Aug. 21, 2013) abstract.
Whatman Product Guide, 2 pages (1997).
Wu, M. et al., Self-assembling peptide nanofibrous hydrogel on immediate hemostasis and accelerative osteosis, Biomacromolecules, 16: 3112-3118 (2015).
Yamamoto, H. et al, A novel method of endoscopic mucosal resection using sodium hyaluronate, Gastrointestinal Endoscopy, 50(2): 251-256 (1999).
Yokoi, H. et al., Dynamic reassembly of peptide RADA16 nanofiber scaffold, Proc. Natl. Acad. Sci. U S A, 102(24):8414-9 (2005).
Yoshida, M, et al., Initial clinical trial of a novel hemostat, TDM-621, in the endoscopic treatments of the gastric tumors, J. Gastroenterol Hepatol., 29: 77-79 (2014).
Zhang, S. Self-assembling peptide materials, Amino Acids, Pept. Proteins, 37:40-65 (2012).
Zhang, S., Beyond the Petri dish, Nat. Biotechnol., 22(2):151-2 (2004).
Zhang, S., Designer Self-Assembling Peptide Nanofiber Scaffolds for Study of 3☐D Cell Biology and Beyond, Cancer Research, 335-362 (2008).
Zhang, S., Fabrication of novel biomaterials through molecular self-assembly, Nat. Biotechnol., 21(10):1171-8 (2003).
Zhaoyang, Y. et al., Temperature and pH effects on biophysical and morphological properties of self-assembling peptide RADA16-T, Journal of Peptide Science, 14(2):152-162 (2008).
Zhou, X-R. et al., Self-assembly of PH and calcium dual-responsive peptide-amphiphilic hydrogel, Journal of Peptide Science, 19: 737-744 (2013).
Paradís-Bas, M. et al, RADA-16: A Tough Peptide—Strategies for Synthesis and Purification, Eur. J. Org. Chem., 5871-5878 (2013).

* cited by examiner

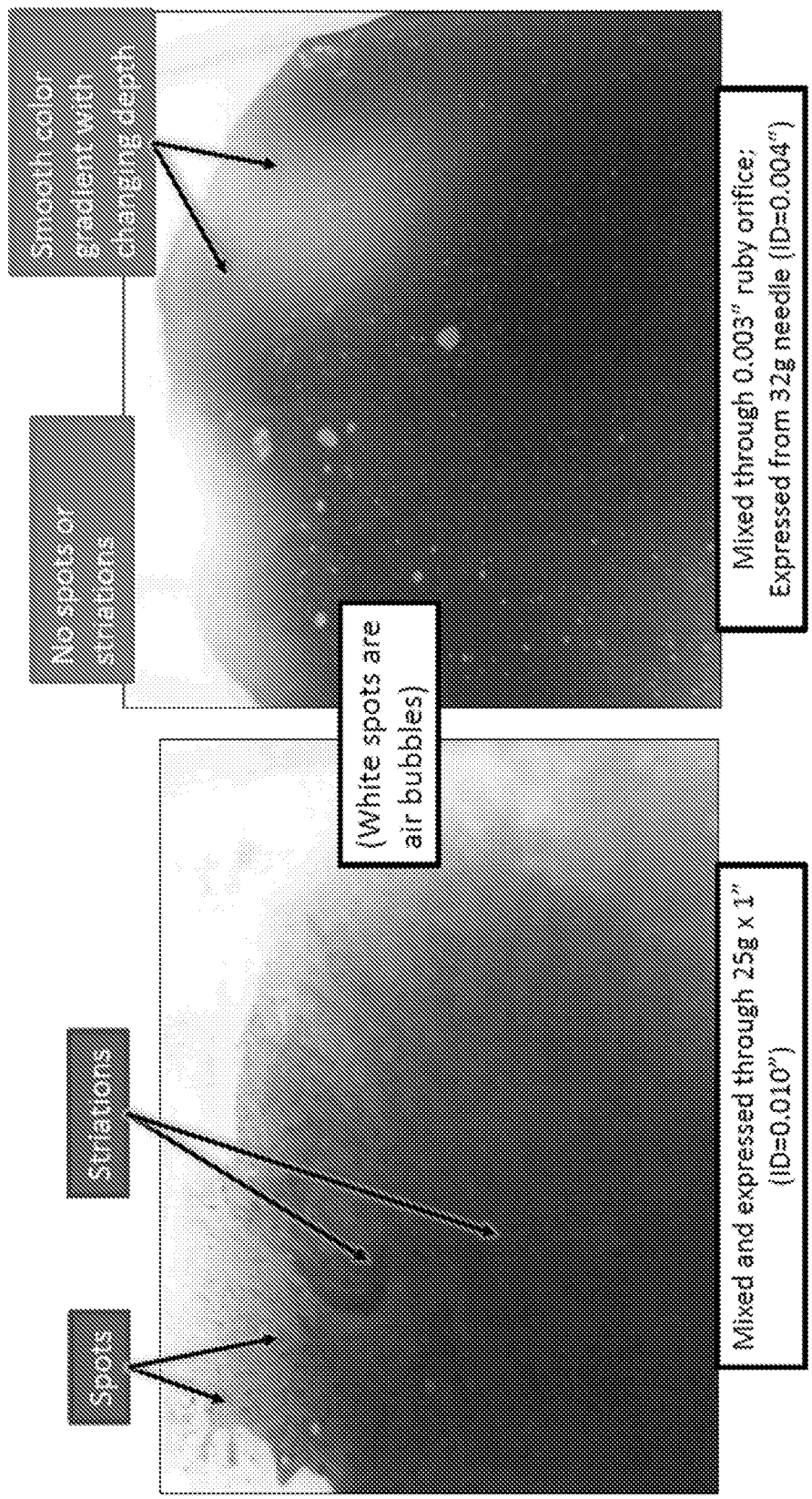

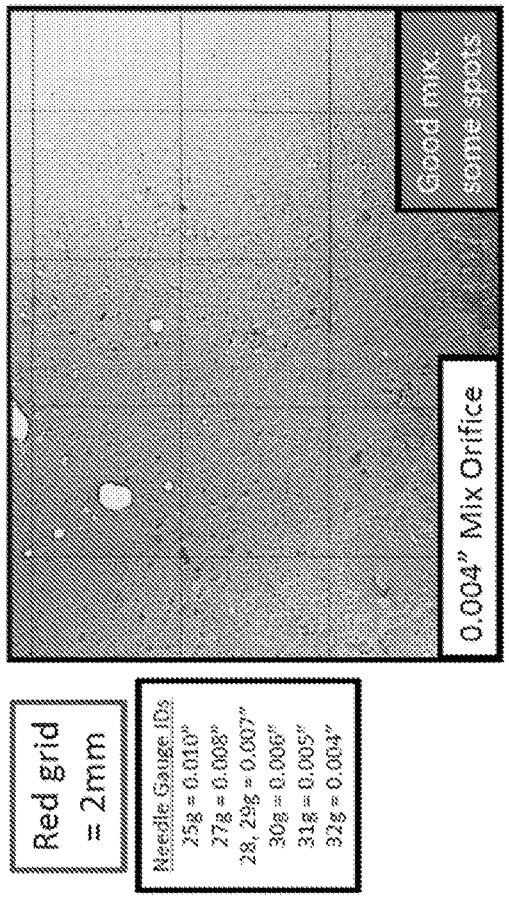
Fig. 7A — 0.003" Mix Orifice — Superb mix
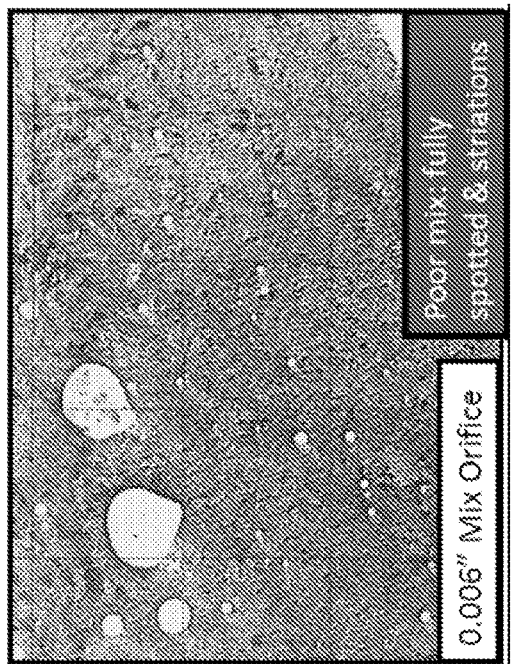
Fig. 7B — 0.004" Mix Orifice — Good mix, some spots
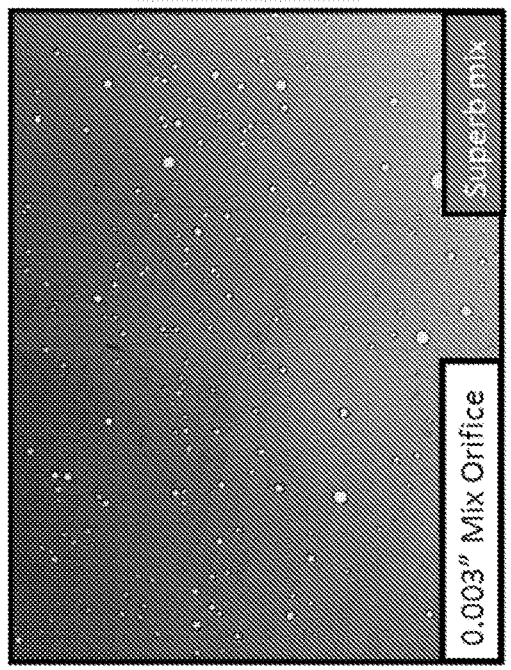
Fig. 7C — 0.005" Mix Orifice — OK mix, larger spots, minor striations
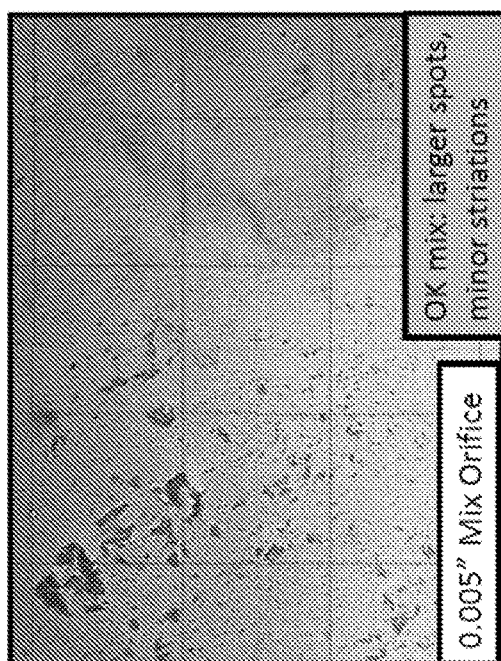
Fig. 7D — 0.006" Mix Orifice — Poor mix (fully spotted & striations)
Red grid = 2mm
Needle Gauge IDs:
25g = 0.010"
27g = 0.008"
28, 29g = 0.007"
30g = 0.006"
31g = 0.005"
32g = 0.004"

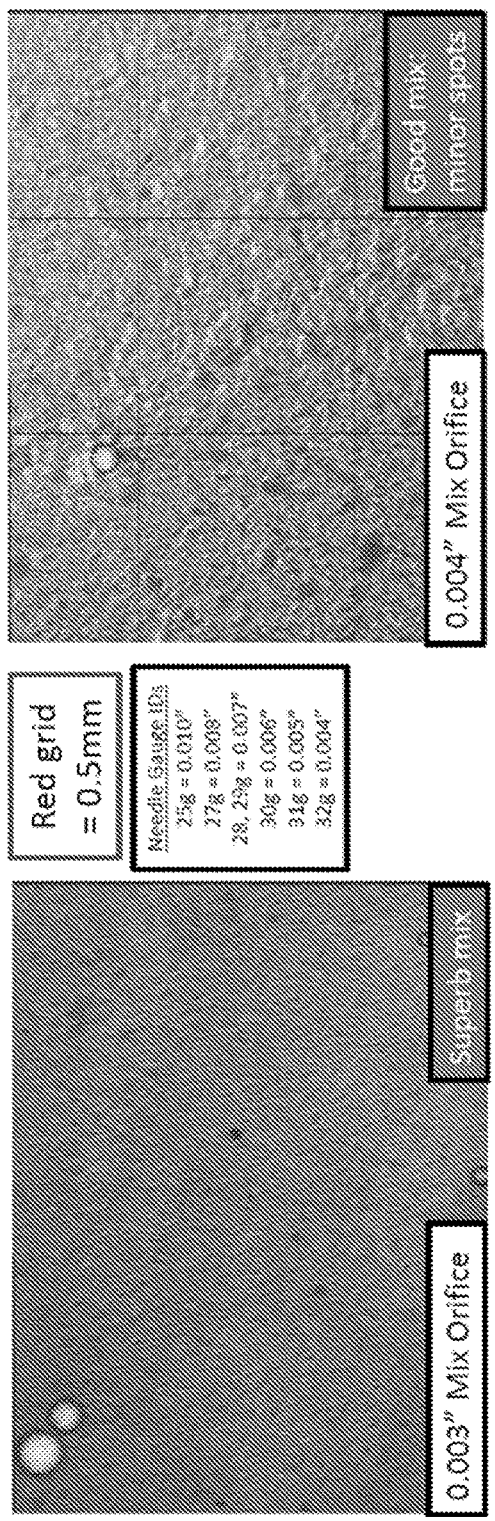
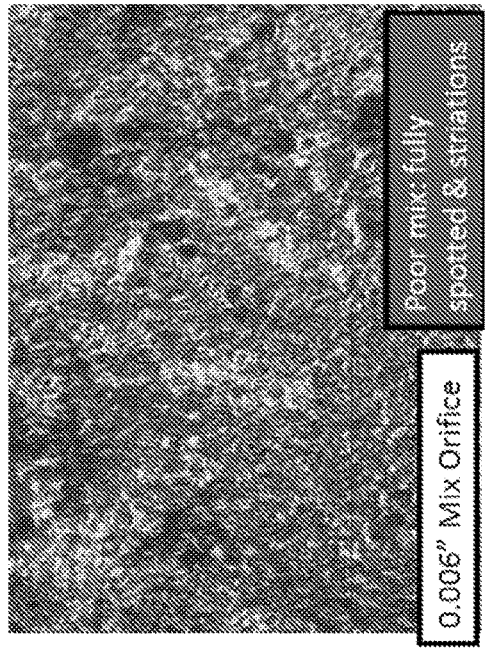
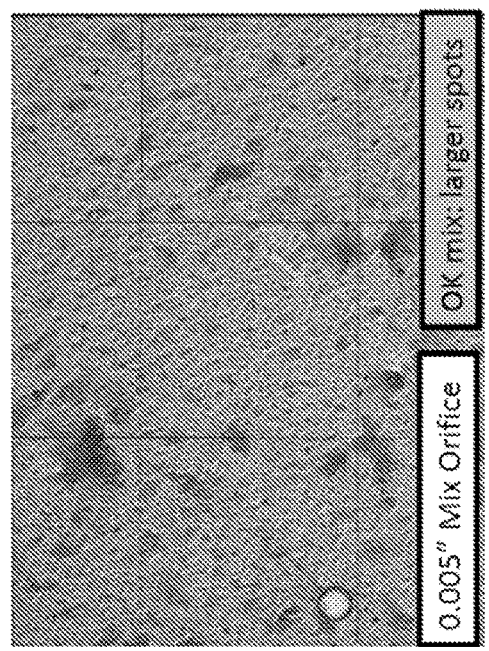
Fig. 8A  Fig. 8B  Fig. 8C  Fig. 8D

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: synthetic

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Lys Leu Asp Leu Lys Leu Asp Leu Lys Leu Asp Leu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Ile Glu Ile Lys Ile Glu Ile Lys Ile Glu Ile Lys Ile
1               5                   10

<210> SEQ ID NO 4
<211> LENGTH: 4
<212> TYPE: PRT
<213> ORGANISM: Artificial Sequence
```

```
<220> FEATURE:
<223> OTHER INFORMATION: synthetic

<400> SEQUENCE: 4

Arg Ala Asp Ala
1

<210> SEQ ID NO 5
<211> LENGTH: 4
<212> TYPE: PRT
<213> ORGANISM: Artificial Sequence
<220> FEATURE:
<223> OTHER INFORMATION: synthetic

<400> SEQUENCE: 5

Lys Leu Asp Leu
1

<210> SEQ ID NO 6
<211> LENGTH: 4
<212> TYPE: PRT
<213> ORGANISM: Artificial Sequence
<220> FEATURE:
<223> OTHER INFORMATION: synthetic

<400> SEQUENCE: 6

Ile Glu Ile Lys
1
```

COMBINATION COMPOSITIONS

CROSS REFERENCE TO RELATED APPLICATIONS

This application is a U.S. National State Application filed under 35 U.S.C. § 371 based on International Application No. PCT/US2016/069133, filed Dec. 29, 2016, which claims the benefit of U.S. Provisional Application No. 62/275,752, filed Jan. 6, 2016, the entire contents of each of which are herein incorporated by reference.

SEQUENCE LISTING

This application makes reference to a sequence listing submitted in electronic form as an ascii.txt file named "2004837-0153_Sequences.txt". The .txt file was generated on Jun. 19, 2018 and is 1 kb in size. The entire contents of the Sequence Listing are herein incorporated by reference.

BACKGROUND

Peptide agents with the ability to self-assemble into gel structures have a wide variety of uses in therapeutic and research contexts. One such peptide agent, for example, a synthetic, 16-amino acid polypeptide with a repeating sequence of arginine, alanine, and aspartic acid (i.e., RADARADARADARADA[SEQ ID NO:1], also known as "RADA16"), is commercially available under the trade names PuraStat®, PuraMatrix®, and PuraMatrix GMP® from 3-D Matrix Medical Technology, and has demonstrated utility in a wide range of laboratory and clinical applications, including cell culture, drug delivery, accelerated cartilage and bone growth, and regeneration of CNS, soft tissue, and cardiac muscle, and furthermore as a matrix, scaffold, or tether that can be associated with one or more detectable agents, biologically active agents, cells, and/or cellular components.

SUMMARY

The present disclosure provides improved technologies relating to combination compositions comprising self-assembling peptide materials and payload (e.g., therapeutic) agents.

Among other things, the present disclosure is based on identification of a source of a problem that can sometimes arise with certain such combination compositions. The present disclosure specifically documents the discovery that, in some cases, such combination compositions may not have sufficient homogeneity (e.g., with respect to distribution of a payload agent within the composition). The present disclosure also documents the discovery that homogeneous combination compositions can be prepared from compositions (e.g., liquid compositions) of self-assembling peptides by subjecting such compositions of self-assembling peptides to shear stress prior to combining with a payload (e.g., therapeutic) agent.

In one aspect, the present disclosure provides a combination composition comprising (i) self-assembling peptides comprising between about 7 amino acids and 32 amino acids and an amino acid sequence of alternating hydrophobic amino acid and hydrophilic amino acids, and (ii) one or more payload agents (e.g., therapeutic agents), wherein a combination composition has a storage modulus of about 0.1 to about 100 Pa (e.g., at 5 rad/sec of frequency and 0.1 Pa of oscillation stress), and/or the combination composition has a viscosity in the range of about 0.5 Pa·s to about 50,000 Pa·s at room temperature.

In some embodiments, self-assembling peptides of a combination composition comprise RADA16 (SEQ ID NO:1), IEIK13 (SEQ ID NO:3), or KLD12 (SEQ ID NO:2).

In some embodiments, a combination composition comprises a concentration of self-assembling peptides of at least 0.5 wt % (e.g., 0.5 wt %, 1 wt %, 1.5 wt %, 2 wt %, 2.5 wt %, 3 wt %, 3.5 wt %, 4 wt %, 4.5 wt %, 5 wt %, or more).

In some embodiments, one or more payload agents (e.g., therapeutic agents) of a combination composition are distributed substantially homogeneously within the combination composition.

In some embodiments, self-assembling peptides (e.g., substantially all of the self-assembling peptides) of a combination composition have substantially random secondary structure. In some embodiments, self-assembling peptides (e.g., substantially all of the self-assembling peptides) of a combination composition are not substantially arranged in beta sheet conformation.

In some embodiments, one or more payload agents (e.g., therapeutic agents) of a combination composition comprise a small molecule, a polypeptide, a cell, or a tissue.

In some embodiments, a combination composition is substantially free of salt.

In another aspect, the present disclosure provides a method of manufacturing a combination composition, the method comprising (i) homogenizing (e.g., resetting) a liquid peptide composition comprising self-assembling peptides by subjecting the composition to high shear stress, and (ii) combining the homogenized (e.g., reset) composition with one or more payload agents (e.g., therapeutic agents). In some embodiments, the self-assembling peptides comprise between about 7 amino acids and 32 amino acids and an amino acid sequence of alternating hydrophobic amino acid and hydrophilic amino acids. In some embodiments, the combination composition has a storage modulus of about 0.1 to about 100 Pa at 5 rad/sec of frequency and 0.1 Pa of oscillation stress, and/or the combination composition has a viscosity in the range of about 0.5 Pa·s to about 50,000 Pa·s at room temperature.

In some embodiments, the liquid peptide composition has an initial (e.g., prior to step of homogenizing or resetting) storage modulus of about 100 Pa to about 3000 Pa at 5 rad/sec of frequency and 0.1 Pa of oscillation stress, and/or the liquid peptide composition has an initial (e.g., prior to step of homogenizing or resetting) viscosity in the range of about 200 Pa·s to about 50,000 Pa·s at room temperature.

In some embodiments, a combination composition has a storage modulus at a level that is about 0.01% to 80% of its initial storage modulus (e.g., of the initial storage modulus of the liquid peptide composition prior to the step of homogenizing or resetting).

In some embodiment, homogenizing step utilizes at least one (e.g., 2, 3, 4, 5, 6, 7, 8, 9, 10 or more) shear-thinning units.

In some embodiments, at least one shear-thinning unit is or comprises at least one needle. In some embodiments, at least one needle is at least 1 mm long. In some embodiments, at least one needle has a gauge within the range of about 27 to about 32.

In some embodiments, at least one shear-thinning unit is or comprises at least one screen with micro- or nano-sized holes. In some embodiments, micro- or nano-sized holes of the shear-thinning unit have a largest dimension within a range of about 5 μm to about 200 μm.

In some embodiments, the screen is made at least in part of a material selected from the group consisting of stainless-steel, tungsten, titanium, silicon, ceramic, plastic, and combination thereof. In some embodiments, thickness of the screen is about 10 μm to about 10 mm.

In some embodiments, high shear stress is within a range of about 30 to about 200 Pa.

In some embodiments, the liquid peptide composition comprises RADA16 (SEQ ID NO:1), IEIK13 (SEQ ID NO:3), or KLD12 (SEQ ID NO:2). In some embodiments, the liquid peptide composition comprises self-assembling peptides at a concentration of at least 2.5%.

In another aspect, the present disclosure provides a combination composition prepared using any of the methods of the present disclosure. In another aspect, the present disclosure provides a device described herein.

Definitions

In order for the present disclosure to be more readily understood, certain terms are first defined below. Additional definitions for the following terms and other terms are set forth throughout the specification.

The term "agent" as used herein refers to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, and ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety. In some embodiments, an agent is a cell and/or tissue. In some embodiments, an agent is or comprises a cellular lysate. In some embodiments, an agent is or comprises cellular material and/or multi-cellular material (e.g., micro-column grafts and/or micro-grafts).

As used herein, the term "amino acid," in its broadest sense, refers to any compound and/or substance that can be incorporated into a polypeptide chain, e.g., through formation of one or more peptide bonds. In some embodiments, an amino acid has the general structure $H_2N—C(H)(R)—COOH$. In some embodiments, an amino acid is a naturally-occurring amino acid. In some embodiments, an amino acid is a synthetic amino ac id; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Two events or entities are "associated" with one another, as that term is used herein, if the presence, level and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

As used herein, the term "cellular lysate" or "cell lysate" refers to a fluid containing contents of one or more disrupted cells (i.e., cells whose membrane has been disrupted). In some embodiments, a cellular lysate includes both hydrophilic and hydrophobic cellular components. In some embodiments, a cellular lysate is a lysate of one or more cells selected from the group consisting of plant cells, microbial (e.g., bacterial or fungal) cells, animal cells (e.g., mammalian cells), human cells, and combinations thereof. In some embodiments, a cellular lysate is a lysate of one or more abnormal cells, such as cancer cells. In some embodiments, a cellular lysate is a crude lysate in that little or no purification is performed after disruption of the cells, which generates a "primary" lysate. In some embodiments, one or more isolation or purification steps is performed on the primary lysate. However, the term "lysate" refers to a preparation that includes multiple cellular components and not to pure preparations of any individual component.

The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc.) will typically refer to comparisons made under comparable conditions.

By "complementary" is meant capable of forming ionic or hydrogen bonding interactions between hydrophilic residues from adjacent peptides, e.g., in a sheet or scaffold, each hydrophilic residue in a peptide either hydrogen bonds or ionically pairs with a hydrophilic residue on an adjacent peptide or is exposed to solvent.

Certain methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

As used herein, a hydrogel such as a peptide hydrogel is "stable with respect to mechanical or physical agitation" if, when subjected to mechanical agitation, it substantially retains the physical properties (such as elasticity, viscosity, etc.), that characterized the hydrogel prior to physical agitation. The hydrogel need not maintain its shape or size and may fragment into smaller pieces when subjected to mechanical agitation while still being termed stable with respect to mechanical or physical agitation. The term "stable" does not have this meaning except when used with this phrase.

The term "gel" as used herein refers to viscoelastic materials whose rheological properties distinguish them from solutions, solids, etc. In some embodiments, a composition is considered to be a gel if its storage modulus (G') is larger than its modulus (G"). In some embodiments, a composition is considered to be a gel if there are chemical or physical cross-linked networks in solution, which is distinguished from entangled molecules in viscous solution.

The term "in vitro" as used herein refers to events that occur in an artificial environment, e.g., in a test tube or reaction vessel, in cell culture, etc., rather than within a multi-cellular organism.

The term "in vivo" as used herein refers to events that occur within a multi-cellular organism, such as a human and a non-human animal. In the context of cell-based systems, the term may be used to refer to events that occur within a living cell (as opposed to, for example, in vitro systems).

As used herein, the term "nanofiber" refers to a fiber having a diameter of nanoscale dimensions. Typically a nanoscale fiber has a diameter of 500 nm or less. According to certain embodiments of the invention a nanofiber has a diameter of less than 100 nm. According to certain other embodiments of the invention a nanofiber has a diameter of less than 50 nm. According to certain other embodiments of the invention a nanofiber has a diameter of less than 20 nm. According to certain other embodiments of the invention a nanofiber has a diameter of between 10 and 20 nm. According to certain other embodiments of the invention a nanofiber has a diameter of between 5 and 10 nm. According to certain other embodiments of the invention a nanofiber has a diameter of less than 5 nm.

The term "peptide" as used herein refers to a polypeptide that is typically relatively short, for example having a length of less than about 100 amino acids, less than about 50 amino acids, less than 20 amino acids, or less than 10 amino acids.

The term "polypeptide" as used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

The term "pure" is used to indicate the extent to which the peptides described herein are free of other chemical species, including deletion adducts of the peptide in question and peptides of differing lengths.

The term "reference" as used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

The term "self-assembling" is used herein in reference to certain polypeptides that, under appropriate conditions, can spontaneously self-associate into structures so that, for example, solutions (e.g., aqueous solutions) containing them develop gel character. In some embodiments, interactions between and among individual self-assembling polypeptides within a composition are reversible, such that the composition may reversibly transition between a gel state and a solution state. In some embodiments, self-assembly (and/or dis-assembly) is responsive to one or more environmental triggers (e.g., change in one or more of pH, temperature, ionic strength, osmolarity, osmolality, applied pressure, applied shear stress, etc.). In some embodiments, compositions of self-assembling polypeptides are characterized by detectable beta-sheet structure when the polypeptides are in an assembled state. In some embodiments, compositions of self-assembling polypeptides are characterized by detectable random secondary structure when the polypeptides are in a homogeneous state.

By "structurally compatible" is meant capable of maintaining a sufficiently constant intrapeptide distance to allow scaffold formation. In certain embodiments of the invention the variation in the intrapeptide distance is less than 4, 3, 2, or 1 angstroms. It is also contemplated that larger variations in the intrapeptide distance may not prevent scaffold formation if sufficient stabilizing forces are present. This distance may be calculated based on molecular modeling or based on a simplified procedure that has been previously reported (U.S. Pat. No. 5,670,483). In this method, the intrapeptide distance is calculated by taking the sum of the number of unbranched atoms on the side-chains of each amino acid in a pair. For example, the intrapeptide distance for a lysine-glutamic acid ionic pair is 5+4=9 atoms, and the distance for a glutamine-glutamine hydrogen bonding pair is 4+4=8 atoms. Using a conversion factor of 3 angstroms per atom, the variation in the intrapeptide distance of peptides having lysine-glutamic acid pairs and glutamine-glutamine pairs (e.g., 9 versus 8 atoms) is 3 angstroms.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

As used herein, a "therapeutically effective amount" is an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Unless defined otherwise, technical and scientific terms have the same meaning as commonly understood by one of ordinary skill in the art to which this invention belongs.

All references cited herein, including patent applications and publications, are incorporated by reference in their entirety.

BRIEF DESCRIPTION OF THE DRAWING

The Drawing, which is comprised of at least the following Figures, is for illustration purposes only, not for limitation.

FIG. 3A depicts a barrel system with dual syringes. FIG. 3C depicts a luer lock connector system with two syringes (e.g., needle gauge of 25 G or 27 G). The solutions in FIGS. 3B (mixed by the system in FIG. 3A) and 3D (mixed by the system in FIG. 3B) leach Congo Red out. The solutions in FIGS. 3B and 3D are not mixed homogeneously.

FIGS. 6A and 6B are optical images of the solutions shown in FIG. 5. The solutions were placed on slide glass and covered with cover glass.

FIGS. 7A-7D are optical microscopy images of the solutions treated with various sizes of needles. The magnification is 27×.

FIGS. 8A-8D are optical microscopy images of the solutions treated with various sizes of needles. The magnification is 164×.

DETAILED DESCRIPTION

Figure 1:
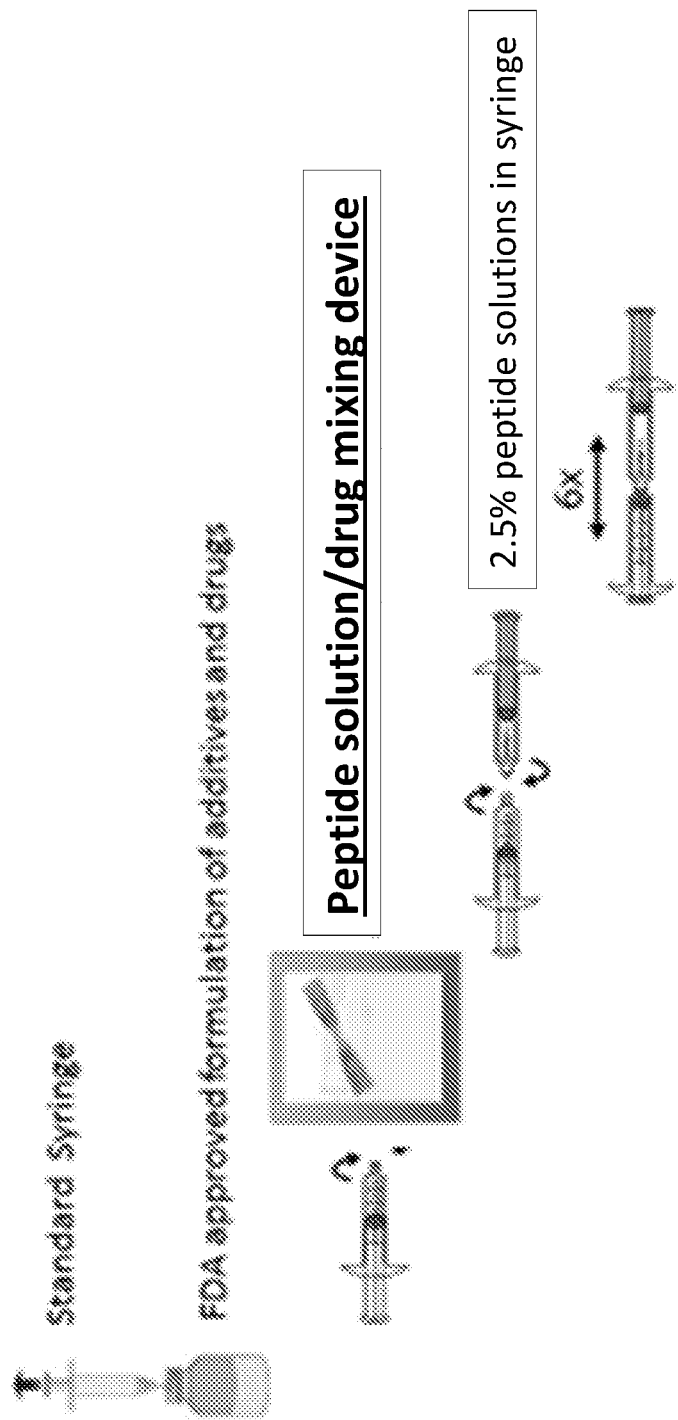
FIG. 1 illustrates an exemplary process to reset and mix a peptide solution with a drug.

The present disclosure relates, in part, to specific preparations of synthetic self-assembling peptide scaffolds as biocompatible and biodegradable materials for therapeutic delivery of payload agents (e.g., drugs, growth factors, cells and/or tissues). The present disclosure encompasses the discovery that purified self-assembling peptides can be prepared in a manner that, in certain instances, facilitates delivery of therapeutic combination products such that the self-assembling peptide scaffold composition has an altered form that allows for homogeneous mixing and application of payload agents.

Scaffolds produced from self-assemblies of amphiphilic peptides (e.g., peptides with alternating hydrophobic and hydrophilic residues) have several interesting properties: they are highly viscous, yet transparent, and non-cytotoxic. Furthermore, safety and biocompatibility tests have shown that these materials, when implanted into animals or tested in vitro, demonstrate superior safety and biocompatibility characteristics to other scaffold products in the medical market place. Additionally, these viscous peptides do not clog catheters and syringes due to their viscosity; rather, the material remains both flowable and injectable.

Among other things, the present disclosure identifies the source of a problem with self-assembling peptides when mixing with payloads (e.g., therapeutic agents) and/or when producing combination compositions of such self-assembling peptides and payloads having sufficient viscosity for certain applications. Specifically, in the process of developing combination compositions comprising peptides and payload agents, it was discovered that sometimes it was challenging to obtain well-mixed and evenly distributed, e.g., homogeneous, compositions. Upon further examination, it was discovered that in certain instances, compositions of self-assembling peptides were not homogeneous after storage and prior to combining with a payload agent. Furthermore, freshly produced compositions of self-assembling peptides, which are therefore likely to be more homogenous than stored peptide solutions, do not always demonstrate sufficient levels of viscosity or stiffness for certain applications.

The present invention encompasses the discovery that preparation of a homogenous self-assembling peptide solution, e.g., from a stored composition of such self-assembling peptides, with an elevated level of viscosity above freshly-prepared self-assembling peptide solution enables properly-mixed combination compositions, such that payloads would be evenly (e.g., homogenously) distributed within peptide solutions, and also such that combination compositions would demonstrate an optimal/effective viscosity for intended applications.

Peptides and Peptide Compositions

In accordance with one or more embodiments, peptide compositions may include an amphiphilic polypeptide having about 6 to about 200 amino acid residues. In certain embodiments, the may have a length of at least about 7 amino acids. In certain embodiments, the polypeptides may have a length of between about 7 to about 17 amino acids. In certain embodiments, the polypeptides may have a length of at least 8 amino acids, at least about 12 amino acids, or at least about 16 amino acids.

In some embodiments, as is understood in the art, an amphiphilic polypeptide is one whose sequence includes both hydrophilic amino acids and hydrophobic amino acids. In some embodiments, such hydrophilic amino acids and hydrophobic amino acids may be alternately bonded, so that the peptide has an amino acid sequence of alternating hydrophilic and hydrophobic amino acids. In some embodiments, a polypeptide for use in accordance with the present disclosure has an amino acid sequence that comprises or consists of repeated units of the sequence Arg-Ala-Asp-Ala (RADA; SEQ ID NO:4). In some embodiments, a polypeptide for use in accordance with the present disclosure has an amino acid sequence that comprises or consists of repeated units of the sequence Lys-Leu-Asp-Leu (KLDL; SEQ ID NO:5). In some embodiments, a polypeptide for use in accordance with the present disclosure has an amino acid sequence that comprises or consists of repeated units of the sequence Ile-Glu-Ile-Lys (IEIK; SEQ ID NO:6).

In some embodiments, a peptide for use in accordance with the present disclosure, may generally be self-assembling, and/or may exhibit a beta-sheet structure in aqueous solution under certain conditions. In some embodiments, a peptide for use in accordance with the present disclosure, may generally be self-assembling, and/or may exhibit a random secondary structure in aqueous solution under certain conditions.

In some embodiments, a peptide for use in accordance with the present disclosure has an amino acid sequence: Arg-Ala-Asp-Ala-Arg-Ala-Asp-Ala-Arg-Ala-Asp-Ala-Ala-Asp-Ala (i.e., RADA16, aka (RADA)$_4$; SEQ ID NO:1). In some embodiments, a peptide for use in accordance with the present disclosure has an amino acid sequence: Lys-Leu-Asp-Leu-Lys-Leu-Asp-Leu-Lys-Leu-Asp-Leu (i.e., KLDL12, aka (KLDL)$_3$ aka KLD12; SEQ ID NO: 2). a peptide for use in accordance with the present disclosure has an amino acid sequence: Ile-Glu-Ile-Lys-Ile-Glu-Ile-Lys-Ile-Glu-Ile-Lys-Ile (i.e., IEIK13, aka (IEIK)$_3$I; SEQ ID NO:3).

Those skilled in the art, reading the present specification, will appreciate that any of a variety of other peptides may alternatively be employed in the practice of the present invention. In some embodiments, for example, one or more peptides as described in US Patent Application Publication No. 2009/0111734 A1, US Patent Application Publication No. 2008/0032934 A1, US Patent Application Publication No. 2014/0038909 A1, U.S. Pat. No. 7,846,891 B2, U.S. Pat. No. 7,713,923 B2, U.S. Pat. No. 5,670,483 B2, the relevant contents of which are incorporated herein by reference.

In some embodiments, a peptide for use in accordance with the present invention have an amino acid sequence that comprises or consists of a sequence represented by one of the following formulae:

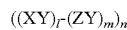  Formula (a)

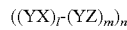  Formula (b)

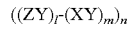  Formula (c)

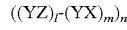  Formula (d), wherein X represents an acidic amino acid, Y represents a hydrophobic amino acid and Z represents a basic amino acid, and l, m and n are all integers (n(l+m)<200), (1≤n≤100)).

In some embodiments, peptide concentration in a combination composition described herein is at least 0.05 wt %, at least 0.25 wt %, at least 0.5 wt %, at least 0.75 wt %, at least 1.0 wt % or more. In some embodiments, peptide concentration in a combination composition described herein is less than 5 wt %, less than 4.5 wt %, less than 4 wt %, less than 3.5 wt %, less than 3 wt %, or less. In some embodiments, peptide concentration in a combination composition described herein is within a range between about 0.5 wt % and about 3 wt %. In some embodiments, peptide concentration in a combination composition described herein is within a range between about 0.5 wt % and about 2.5 wt %. In some embodiments, peptide concentration in a combination composition described herein is within a range between about 1 wt % and about 3 wt %. In some embodiments, peptide concentration in a combination composition described herein is within a range between about 1% and about 2.5 wt %. In some embodiments, peptide concentration in a combination composition described herein is about 0.5 wt %, about 1 wt %, about 1.5 wt %, about 2 wt %, about 2.5 wt %, about 3 wt %, or more.

In some particular embodiments, where the peptide is RADA16 (SEQ ID NO:1), peptide concentration in a combination composition described herein is within a range of about 0.05 wt % to about 10 wt %.

In some particular embodiments, where the peptide is KLD12 (SEQ ID NO:2), peptide concentration in a combination composition described herein is within a range of about 0.05 wt % to about 10 wt %.

In some particular embodiments, where the peptide is IEIK13 (SEQ ID NO:3), peptide concentration in a combination composition described herein is within a range of about 0.05 wt % to about 10 wt %.

Payload Agents

In some particular embodiments, combination compositions of the invention comprise one or more payload agents, e.g., therapeutic agents or detection agents. Such agents include, e.g., a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules (e.g. antibiotics, anticancer drugs, antipain drugs, anti-inflammatory drugs, steroids, anti-psychotics), antibodies, antibody fragments, aptamers, nucleic acids (e.g., siRNAs, shRNAs, DNA/RNA hybrids, antisense oligonucleotides, ribozymes), peptides, peptide mimetics, proteins, fusion proteins, vaccines, anti-coagulants, cytokines, hormones, enzymes, blood factors, extracellular matrix components, etc. In some embodiments, an agent may be selected from the group consisting of micrograft tissue, drugs (e.g., antibiotics), and biologics (e.g., growth factors and/or other molecules/proteins). In some embodiments, an agent is a cytokine (e.g., epidermal growth factor, nerve growth factor, transforming growth factor-alpha and beta, platelet-derived growth factor, insulin-like growth factor, vascular endothelial growth factor).

Detection agents may refer to any element, molecule, functional group, compound, fragment or moiety that is detectable. In some embodiments, a detection entity is provided or utilized alone. In some embodiments, a detection entity is provided and/or utilized in association with (e.g., joined to) another agent. Examples of detection entities include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

In some embodiment, an agent is about 1 Å to about 500 μm. In some embodiment, an agent is about 1 nm to about 500 μm. In some embodiment, an agent is about 10 nm to about 500 μm. In some embodiment, an agent is about 100 nm to about 500 μm. In some embodiment, an agent is about 1 μm to about 500 μm. In some embodiment, an agent is about 10 μm to about 500 μm. In some embodiment, an agent is about 100 μm to about 500 μm. In some embodiment, an agent is about 1 Å to about 100 μm. In some embodiment, an agent is about 1 Å to about 10 μm. In some embodiment, an agent is about 1 Å to about 1 μm. In some embodiment, an agent is about 1 Å to about 100 nm. In some embodiment, an agent is about 1 Å to about 1 nm.

In some embodiments, an agent may be water soluble, soluble in an aqueous peptide solution, and/or soluble in an aqueous peptide solution comprising one or more additional agents.

Combination Compositions

In some embodiments, combination compositions of the present disclosure may be characterized by exhibiting homogeneous (e.g., substantially homogeneous) distribution of payload agents and self-assembling peptides. In some embodiments, homogeneous distribution of payload agents and peptides (e.g., homogeneity) may be characterized by size of aggregates in the compositions. In some embodiments, homogeneous peptide solutions and/or combination compositions may have aggregates (e.g., aggregates may comprise peptides, payloads, etc.) having size (e.g., average aggregate size) of no greater than 40 μm, 50 μm, 60 μm, 70 μm, 80 μm, 90 μm, or 100 μm. Size of aggregates may be observed with optical microscope (e.g., magnification of 27×, 164×).

In some embodiments, combination compositions described herein exhibit a high level of self-assembled peptides having random secondary structure. For example, in some embodiments, more than 10%, 20%, 30%, 40%, 50%, 60%, 70%, 80%, 90%, or about 100% of self-assembled peptides in combination compositions described herein have random secondary structure. In some embodiments, number of self-assembled peptides having random secondary structure can be visualized (e.g., measured and/or quantitated visually). For example, number of self-assembled peptide having random secondary structure can be determined (e.g., measured) using microscopy.

In some embodiments, combination compositions described herein exhibit a low level of self-assembled peptides arranged in beta sheet conformation. For example, in some embodiments, less than 90%, 80%, 70%, 60%, 50%, 40%, 30%, 20%, 10%, 5%, or less, of self-assembled peptides in combination compositions described herein are arranged in beta sheet conformation.

In some embodiments, peptide solutions and/or combination compositions in accordance with the present disclosure may be characterized by particular rheological properties. In some embodiments, such rheological properties may include storage modulus, viscosity, etc. In some embodiments, one or more rheological properties may be tested and/or determined (e.g., measured); in some embodiments, one or more rheological properties may be assessed by optical/visual observation.

In some embodiments, relevant optical properties may include one or more of degree of transparency, optical clarity, etc. In some embodiments, one or more optical properties may be tested and/or determined (e.g., measured); in some embodiments, one or more optical properties may be assessed by visual observation. In some embodiments, optical clarity of particular combination compositions may be described as clear, slightly cloudy, or cloudy. In some embodiments, provided combination compositions are clear.

In some embodiments, homogeneity of peptide solutions and/or combination compositions in accordance with the present disclosure have a storage modulus of about 5 to about 100 Pa, e.g., at about 5 rad/sec of frequency and 0.1 Pa of oscillation stress. In some embodiments, homogeneity of peptide solutions and/or combination compositions in accordance with the present disclosure have a storage modulus of about 10, 20, 30, 40, 50, 60, 70, 80, 90, 100, 150, or 200 Pa, e.g., at about 5 rad/sec of frequency and 0.1 Pa of oscillation stress.

In some embodiments, homogeneous peptide solutions and/or combination compositions in accordance with the present disclosure have a storage modulus of about 0.01 to about 1000 Pa, about 0.01 to about 750 Pa, about 0.01 to about 500 Pa, about 0.01 to about 250 Pa, about 0.01 to about 100 Pa, about 0.01 to about 50 Pa, about 1 to about 1000 Pa, about 5 to about 1000 Pa, about 10 to about 1000 Pa, about 1 to about 500 Pa, about 1 to about 250 Pa, about 5 to about 250 Pa, or about 10 to about 250 Pa at 5 rad/sec of frequency and 0.1 Pa of oscillation stress.

In some embodiments, homogeneous peptide solutions and/or combination compositions may have a storage modulus that is about 0.01% to 80% of that of a corresponding stored/aged composition (e.g., a corresponding liquid composition comprising self-assembling peptides and not comprising a payload agent). In some embodiments, a corresponding stored/aged composition is stored/aged at least about 6 hours, 12 hours, 24 hours, 2 days, 3, days, 4 days, 5 days, 6 days, 7 days, 2 weeks, 3 weeks, 1 month, 2 months, 3 months, 4 months, 5 months, 6 months, 1 year, or more. In some embodiments, homogeneous peptide solutions and/ or combination compositions may have a storage modulus that is about 0.01%, 0.05%, 0.1%, 0.5%, 1%, 5%, 10%, 15%, 20%, 25%, 30%, 35%, 40%, 45%, 50%, 55%, 60%, 65%, 70%, 75%, or 80% of that of a corresponding stored/ aged composition.

In some embodiments, homogeneous peptide solutions and/or combination compositions in accordance with the present disclosure have a viscosity in the range of about 0.1 Pa·s to about 100,000 Pa·s, about 0.1 Pa·s to about 75,000 Pa·s, about 0.1 Pa·s to about 50,000 Pa·s, about 0.1 Pa·s to about 25,000 Pa·s, about 0.5 Pa·s to about 100,000 Pa·s, about 0.5 Pa·s to about 75,000 Pa·s, about 0.5 Pa·s to about 50,000 Pa·s, about 0.5 Pa·s to about 25,000 Pa·s, about 1 Pa·s to about 100,000 Pa·s, about 1 Pa·s to about 75,000 Pa·s, about 1 Pa·s to about 50,000 Pa·s, about 1 Pa·s to about 25,000 Pa·s, about 10 Pa·s to about 100,000 Pa·s, about 10 Pa·s to about 75,000 Pa·s, about 10 Pa·s to about 50,000 Pa·s, or about 10 Pa·s to about 25,000 Pa·s at room temperature.

In some embodiments, homogeneous peptide solutions and/or combination compositions may have a viscosity that is about 0.01% to 80% of that of a corresponding stored/aged composition (e.g., a corresponding liquid composition comprising self-assembling peptides and not comprising a payload agent). In some embodiments, a corresponding stored/aged composition is stored/aged at least about 6 hours, 12 hours, 24 hours, 2 days, 3, days, 4 days, 5 days, 6 days, 7 days, 2 weeks, 3 weeks, 1 month, 2 months, 3 months, 4 months, 5 months, 6 months, 1 year, or more. In some embodiments, homogeneous peptide solutions and/or combination compositions may have a viscosity that is about 0.01%, 0.05%, 0.1%, 0.5%, 1%, 5%, 10%, 15%, 20%, 25%, 30%, 35%, 40%, 45%, 50%, 55%, 60%, 65%, 70%, 75%, or 80% of that of a corresponding stored/aged composition (e.g., a corresponding liquid composition comprising self-assembling peptides and not comprising a payload agent).

In some embodiments, homogeneous peptide solutions and/or combination compositions in accordance with the present disclosure comprise a concentration of self-assembling peptides of at least 0.5 wt %, 0.6 wt %, 0.7 wt %, 0.8 wt %, 0.9 wt %, or 1 wt %.

In some embodiments, combination compositions of the invention comprise $10^{-10}$ wt % to about 10 wt %, $10^{-9}$ wt % to about 10 wt %, $10^{-8}$ wt % to about 10 wt %, $10^{-7}$ wt % to about 10 wt %, $10^{-5}$ wt % to about 10 wt %, $10^{-4}$ wt % to about 10 wt %, $10^{-3}$ wt % to about 10 wt %, 0.01 wt % to about 10 wt %, 0.1 wt % to about 10 wt %, or 1 wt % to about 10 wt % of one or more agents. In some embodiments, combination compositions of the invention comprise 0.01 wt % to about 5 wt %, 0.1 wt % to about 5 wt %, or 1 wt % to about 5 wt % of one or more agents. In some embodiments, combination compositions of the invention comprise 0.01 wt % to about 3 wt %, 0.1 wt % to about 3 wt %, or 1 wt % to about 3 wt % of one or more agents. In some embodiments, combination compositions of the invention comprise 0.01 wt % to about 2 wt %, 0.1 wt % to about 2 wt %, or 1 wt % to about 2 wt % of one or more agents.

Peptide Preparations

Fresh Preparation of a Peptide Solution (Dissolution) from a Dried Peptide

In some embodiments, a combination composition described herein comprises a peptide preparation, e.g., a freshly prepared peptide preparation. Synthesized peptides can be prepared according to manufacturer specification and can be stored after synthesis in a dried form (e.g., lyophilized). To create peptide solutions, dried peptides can be dissolved in a solvent (e.g., water) at a concentration suitable for the ultimate use/administration.

In the broadest embodiment, dissolution begins by mixing powdered peptides with water. The peptides are dissolved so that the concentration of peptides is the concentration of the peptides in solution for the final application and/or end use. Final applications or end uses of the peptide solution may influence or determine the concentration at which the peptides are dissolved in solution.

In some embodiments, peptide power is added to a premeasured amount of water. In some embodiments, peptide power is added slowly or in steps so that one addition of peptides is fully dissolved before a subsequent amount of peptide power is added. In some embodiments, water is added to peptide power.

During dissolution, the solution can be stirred. In some embodiments, the mixer used includes an axial or radial flow impeller and/or a propeller, paddle or turbine shaped impeller. In some embodiments, the mixer is operated at a rate of not less than about 500 rpm, but is brought up to that speed slowly from a stopped speed. For example, the mixer starts at a speed of about 200 rpm as the peptide power is added. Once all of the powder is dissolved the mixer speed is increased to about 500 rpm. The rotational speed of the mixer can range from about 30 rpm to about 1000 rpm. Those of skill will appreciate that the speed of the mixer depends in large part on the volume of the mixing vessel and according to the speed of the impeller, which in turn depends on the diameter of the impeller. Where v=speed of the impeller and d=the diameter of the impeller, r=rotational speed, the speed can be calculated by $v=\pi*d*r$, and should be keep proportional as the vessel size is scaled up.

Once at this speed, mixing can continue for about 30 minutes. The rate of mixer speed can be maintained so that the solution is not sheared to such a degree that droplets of the solution are produced from the bulk solution and thrown against the wall of the mixing vessel. The surface of the solution should be continuous, though it does not need to be level, or planar.

During the stirring and dissolution samples can be taken from the mixing tank and inspected to monitor the dissolution. The samples can be centrifuged to remove any entrained gases. The samples are then visually inspected to ensure dissolution of the peptides, also can be examined with content of dissolved peptide by photometer. If inspection indicates undissolved powder, stirring time can be extended.

If the solution is substantially completely dissolved, the solution may be deaerated. Deaeration is equivalent to degassing, which is a process in which a dissolved or entrained gas is removed from a liquid, or its quantity in the liquid reduced. The deaerating step can be performed by any acceptable deaerating method. For example, by vacuum, centrifugation, vibration, liquid-gas membrane separation or allowing the solution to degas naturally. In some embodiments, the deaerating step is performed by vacuum.

In some embodiments, solutions are stirred during aeration. In some embodiments, solutions are stirred at a rate of approximately 50 rpm, 100 rpm, 150 rpm, 200 rpm, 250 rpm, 300 rpm, 350 rpm, 400 rpm or 500 rpm. In some embodiments, it is preferable that the peptide solution that has been heated when it is introduced into the deaeration chamber. Such heating may reduce the viscosity of the solution, improving deaeration efficiency. Caution should be taken in heating as some peptides are subject to degradation with heat and therefore heating may not be appropriate in all circumstances.

Stirring can be combined with pressure reduction to efficiently deaerate from viscous peptide mixture but fast stirring might bring babble into the mixture. To deaerate from peptide mixture, the mixer is operated at a rate of not less than about 300 rpm. Self-assembling peptide mixture becomes gel-like solution during deaeration if stirring is not done at the same time. Mixing self-assembling peptide solution keeps low viscosity so that the solution is effectively deaerated.

The deaerating step can last for at least about 30 minutes. The ultimate length of time for deaerating is dependent on the results, e.g., that the mixture is substantially free of dissolved gas or gas bubbles. During the deaerating samples of the solution are taken and inspected for dissolved gas or bubbles. If dissolved gas or gas bubbles are still present, the degassing process is continued.

After the mixture is sufficiently deaerated, filtration can be performed. Filtration is effective in removing residual debris and other small particles as well as sterilizing the peptide solution in a manner that does not result in degradation of the peptides. Filters retain contaminants using two major types of interactions between filters and contaminant particles. Particles are retained due to their size, and may also be retained due to adsorption to the filter material. Molecular and/or electrical forces between the particles and the filter material attract and retain these entities within the filter.

Generally, the pores of the filter are sized to remove at least a portion of contaminants contained in the peptide solution, retaining the removed dispersed contaminants on the upstream side of the filter (e.g., the inlet side) yielding a filtrate substantially free of contaminants. Specifically the filtrate should not contain contaminants in an amount that would adversely affect the use of the purified peptide solution.

The filtration step is, in some embodiments, performed by filtering through a filter with a specific pore size (e.g., about 0.2 micrometers). The porous membrane includes pores generally having a highly uniform size that is selected depending on the size of the dispersed contaminant to be removed from the liquid mixture. For example, in sterile filtration operations intended to remove microorganisms (while allowing the protein to pass through the filter membrane into the filtrate), the pores preferably have a size in a range of about 0.1 micrometers to about 0.5 micrometers. Suitable filtration systems can also include a primary filter with a pore size of, e.g., 0.2 micrometers, as well as a coarser pre filter to improve throughput and limit accumulation within the finer filter. The coarser pre filter can have a pore size in the range of about 0.4 micrometers to about 10 micrometers. Pre-filter system needs two or more filters so that peptide mixture may be much lost in the pre-filter(s). In addition, tandem pre-filtering system causes to lower the pressure in sterilizing filter, where the initial high pressure is lowered by pre-filter. Highly viscous peptide mixture, such as self-assembling peptide, requires high pressure (0.5 or more MPa) for filtration, so tandem connection of pre-filter and sterilizing filter is not suitable to manufacturing process of viscous self-assembling peptides.

In various embodiments, filtration according to the present invention is performed at a pressure within a range of about 0.3-0.7 MPa.

Those skilled in the art, reading the present specification, will appreciate that any of a variety of fresh-preparation may alternatively be employed in the practice of the present invention. In some embodiments, for example, one or more process conditions (e.g., mixing rate, dimensions of apparatus, etc.) are described in International Patent Application Publication No. WO2014/008400, titled "Fill-Finish Process for Peptide Solutions", the content of which is incorporated by reference herein in its entirety.

In some embodiments, a combination composition described herein is produced from a peptide preparation that has been stored/aged for a period of time. In some such embodiments, a stored/aged peptide solution is reset/homogenized prior to combination with a payload agent, as described herein.

Resetting/Liquefying/Homogenizing a Stored/Aged Peptide Solution

Without wishing to be bound by any particular theory, it is believed that self-assembling peptides form a fibrous three-dimensional structure in aqueous environment as it is energetically favorable than random structures (e.g., due to its amphiphilic property and existing hydrophobic effect in water). Peptides are assembled with next neighboring ones in water to form fibrous nano-structure and this process continues until all peptides are fully assembled to be in the self-assembled composition. However, peptides having fibrous three-dimensional structure may not be appropriate for homogeneous mixing with other components (e.g., payload agents) due to their 3-dimensional hindrance. As described herein, for certain combination compositions of the present disclosure, self-assembling peptides exhibiting a random structure can be used to produce homogenous compositions.

Without wishing to be bound by any particular theory, it is believed that subjecting peptide compositions described herein, prior to combining with a payload agent, to high shear stress can disrupt self-assembled structures (e.g., in freshly prepared and/or stored/aged peptide compositions). In some embodiments, a stored/aged peptide solution (e.g., one comprising self-assembling peptides having beta sheet conformation) may be reset (e.g., homogenized, liquefied, disrupted, etc.) by applying shear stress to the peptide solution. In some embodiment, applied shear stress may reduce storage modulus/viscosity of the solution (e.g., initial storage modulus/viscosity).

In some embodiments, shear stress applied to peptide solutions (e.g., a stored/aged peptide solution) may be at least about 20 Pa. In some embodiments, shear stress applied to peptide solutions may be at least about 30 Pa. In some embodiments, shear stress applied to peptide solutions may be at least about 40 Pa. In some embodiments, shear stress applied to peptide solutions may be at least about 50 Pa. In some embodiments, shear stress applied to peptide solutions may be at least about 60 Pa. In some embodiments, shear stress applied to peptide solutions may be at least about 60 Pa. In some embodiments, shear stress applied to peptide solutions may be at least about 80 Pa. In some embodiments, shear stress applied to peptide solutions may be at least about 90 Pa. In some embodiments, shear stress applied to peptide solutions may be at least about 100 Pa.

In some embodiments, viscosity of peptide composition (e.g., a stored/aged composition described herein) may drop significantly with shear stress. In some embodiments, viscosity of peptides solutions may drop at least 10% with shear stress. In some embodiments, viscosity of peptides solutions may drop at least 30% with shear stress. In some embodiments, viscosity of peptides solutions may drop at least 50% with shear stress. In some embodiments, viscosity of peptides solutions may drop at least 70% with shear stress. In some embodiments, viscosity of peptides solutions may drop at least 90% with shear stress.

In some embodiments, resetting one or more rheological properties is temporary. In some embodiments, the peptide composition is characterized by rheological recovery characteristics. For example, in some embodiments, such compositions are characterized in that one or more of their rheological properties are restored within a time period within a range of about 1 min to about 48 hours.

In some embodiments, peptide compositions may recover their storage modulus (e.g., initial and/or aged/storage modulus) after application of shear stress (e.g., after combining with a payload agent). In some embodiments, peptide solutions may recover about 0.1 to 100% of their original storage modulus in 1 min. In some embodiments, peptide solutions may recover about 0.1 to 10% of their original storage modulus in 1 min. In some embodiments, peptide solutions may recover about 20 to 100% of their original storage modulus in 20 min. In some embodiments, peptide solutions may recover about 20 to 60% of their original storage modulus in 20 min.

In some embodiments, peptide solutions may recover their viscosity over time after combination with a payload agent. In some embodiments, peptide solutions may recover about 0.1 to 30% of their original viscosity in 1 min. In some embodiments, peptide solutions may recover about 0.1 to 100% of their original viscosity in 1 min. In some embodiments, peptide solutions may recover about 20 to 100% of their original viscosity in 20 min. In some embodiments, peptide solutions may recover about 20 to 60% of their original viscosity in 20 min.

In general, as described herein, shear stress may be applied by application of a peptide composition to (and/or passage of a peptide composition through) a shear-thinning unit. In some embodiments, a shear-thinning unit is or comprises a needle, a membrane, and/or a screen. In some embodiments, shear stress may be applied multiple times (e.g., 2 times, 3 times, 4 times, 5 times, 6 times, 7 times, 8 times, 9 times, 10 times). In some embodiments, a stored/aged peptide solution may be contained in one or more syringes before the resetting process. In some embodiments, two syringes may be connected to one shear thinning unit. In some embodiments, the peptide solution may be reset by passing through the unit back and forth.

Needle as a Shear-Thinning Unit

In some non-limiting embodiments, shear stress may be applied by injection through one or more needles. Thus, in some embodiments, one or more needles may be used as a shear-thinning unit.

In some embodiments, a needle may be at least about 1 mm long. In some embodiments, a needle may be at least about 2 mm long. In some embodiments, a needle may be at least about 5 mm long. In some embodiments, a needle may be at least about a 10 mm long. In some embodiments, a needle may be at least about 15 mm long. In some embodiments, a needle may be at least about 20 mm long. In some embodiments, a needle may be at least about 30 mm long. In some embodiments, a needle may be at least about 40 mm long. In some embodiments, a needle may be at least about 50 mm long.

In some embodiments, a needle may have a gauge within a range of about 20 to about 34. In some embodiments, a needle may have a gauge within a range of about 25 to about 34. In some embodiments, a needle may have a gauge of about 27 to about 34. In some embodiments, a needle may have a gauge of about 30 to about 32.

Figure 4:
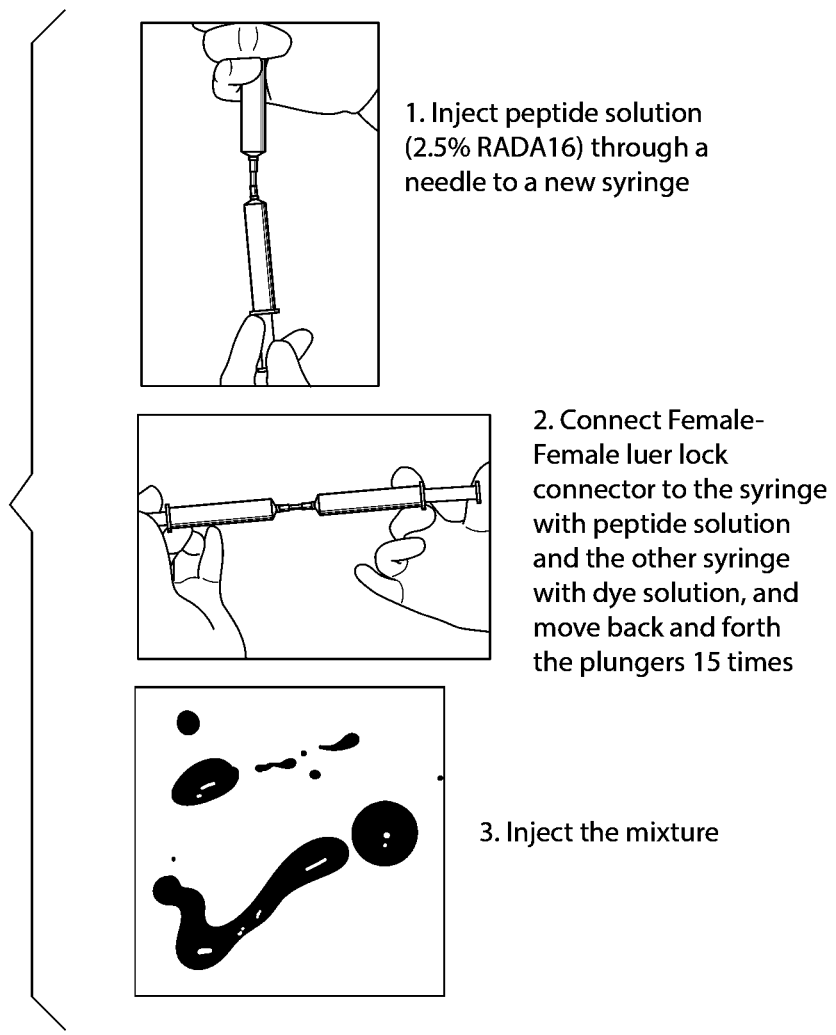
FIG. 4 shows an exemplary process to reset/homogenize a peptide solution (e.g., 2.5% RADA16; SEQ ID NO:1) using a luer lock connector system with two syringes (e.g., needle gauge of 30 G or 32 G), and to mix the solution with a payload solution.
Figure 5:
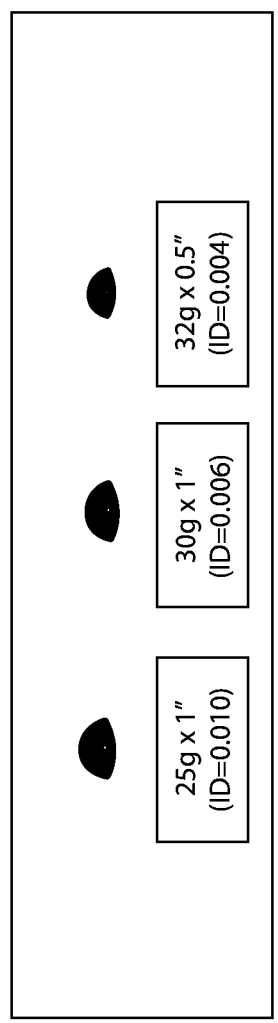
FIG. 5 depicts a solution comprising peptides and Congo Red treated with various sizes of needles. The droplet treated with the bigger needle shows the higher curvature on ⅛" Lexan surface.
Figures 9A, 9B:
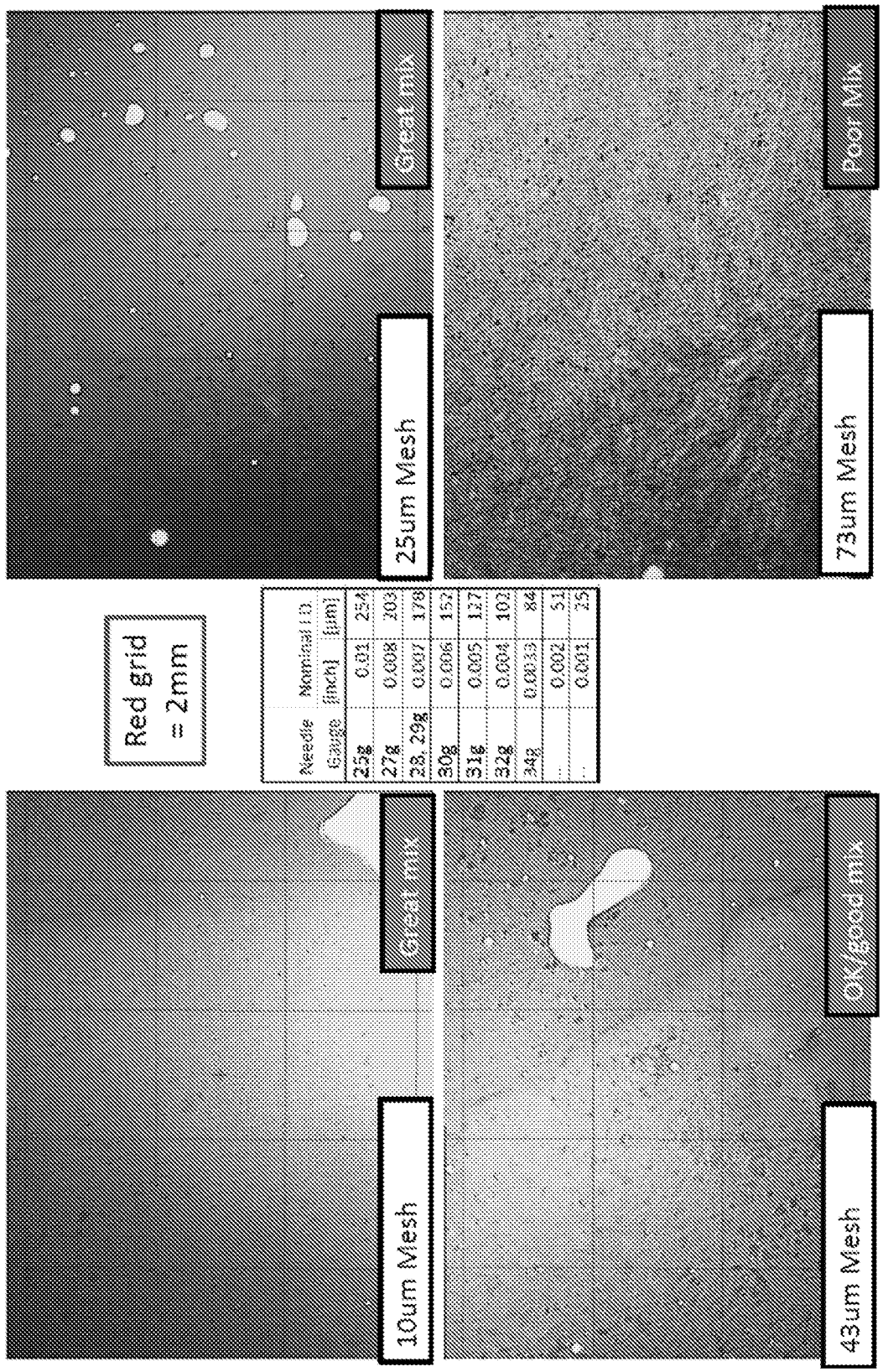
FIGS. 9A-9B are optical microscopy images of the solutions treated with various sizes of meshes. The magnification is 27×.

FIG. 4 discloses one non-limiting embodiment of a process in accordance with one or more non-limiting embodiments. As depicted, peptide composition (e.g., viscous solution of a self-assembling peptide) may be transferred to a first syringe with a needle, coupled and injected to a second syringe containing a payload agent, and mixed.

Membrane as a Shear-Thinning Unit

In some embodiments, a shear-thinning unit utilized to apply shear stress to a peptide composition as described herein may be a device or entity characterized by micro- or nano-pores. In some embodiments, a peptide solution (e.g., a viscous solution of a self-assembling peptide) may be transferred to a dispensing syringe (or a pressure vessel), delivered to a first chamber with pores for shear stress, coupled to and passed (e.g., back and forth) to a second syringe containing a payload agent, and mixed. As will be understood by those skilled in the art, diameter size of membrane may vary depending on the amount of peptide solution.

In some embodiments, pore size of a shear-thinning unit may be about 0.45 µm to 200 µm. In some embodiments, pore size of a shear-thinning unit may be about 1 µm to 150 µm. In some embodiments, pore size of a shear-thinning unit may be about 1 µm to 100 µm. In some embodiments, pore size of a shear-thinning unit may be about 5 µm to 50 µm.

Screen as a Shear-Thinning Unit

In some embodiments, a shear-thinning unit may have micro- or nano-holes. In some embodiments, holes may be patterned or drilled on a plate whose thickness may be about 10 µm to 10 mm in some embodiments. In some embodiments, holes in an embodiment of a shear-thinning unit described herein may have a largest dimension within the range of about may be about 0.5 µm to 200 µm. In some embodiments, such dimension may be within the range of about 0.5 µm to 100 µm. In some embodiments, such dimension may be within the range of about 5 µm to 100 µm. In some embodiments, such dimension may be within the range of about 5 µm to 50 µm.

In some embodiments, a shear-thinning unit of this embodiment may have a pitch between holes within the range of about 5 µm to about 10 mm.

Figure 2:
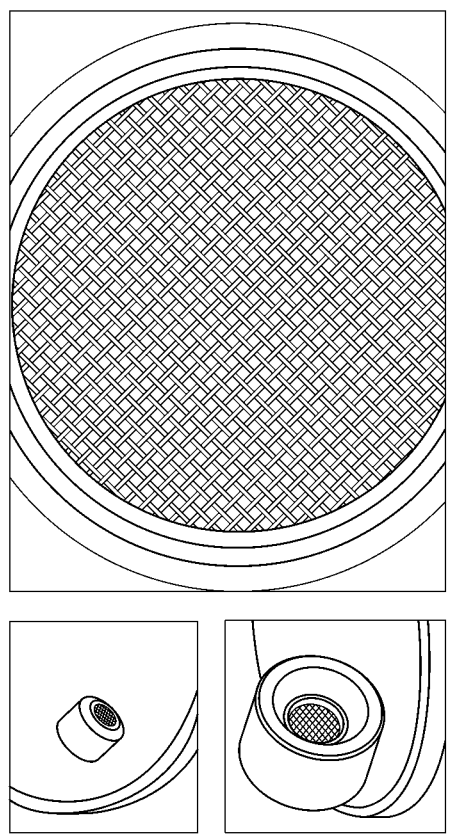
FIG. 2 shows an exemplary shear thinning unit. The mesh of the unit is 43 μm.
Figure 3B:
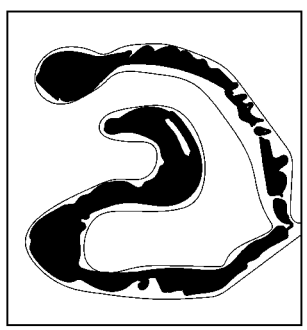
FIGS. 3A-3D show common mixing methods applied to a stored/aged peptide solution and a Congo Red solution, and their results.
Figure 3D:
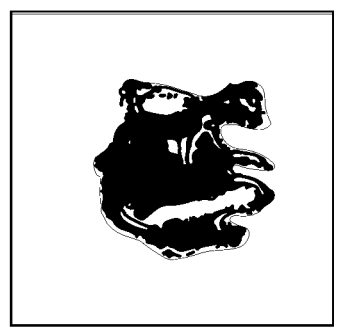
Figure 3A:
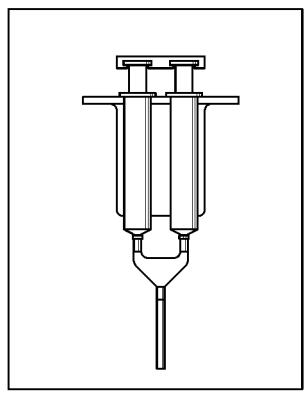
Figure 3C:
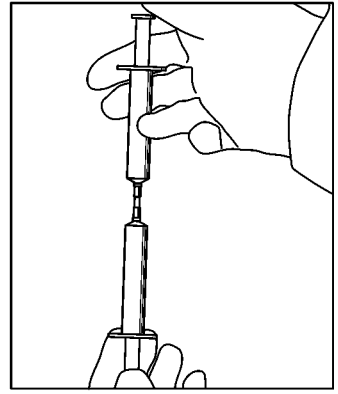

In some embodiments, shear-thinning unit may be made, in whole or in part, of a material selected from the group consisting of stainless-steel, tungsten, titanium, similar metal, silicon, ceramic or plastic materials, and combinations thereof. An exemplary mesh is depicted in FIG. 2.

Mixing a Reset (Liquefied) Peptide Solution and Payloads

In some embodiments, a reset/homogeneous peptide solution may be combined with a payload agent (e.g., a solution containing a payload agent). In some embodiments, a payload agent solution may be mixed in to a reset/homogeneous peptide solution.

FIG. 1 shows an exemplary process to reset and mix a stored/aged solution with a drug solution. A standard syringe can be used to draw up an aliquot of a peptide solution and then it can be homogenized using a mixing device (e.g., shear thinning unit (e.g., needles, meshes)). The syringe can then be connected to a syringe containing a payload agent and mixed multiple times (e.g., 1 time, 2 times, 3 times, 4 times, 5 times, 6 times back and forth).

In an exemplary method, a mixing process can include:
a. Loading a peptide solution and a payload solution each in the their own syringe
b. Attaching a connector and/or adapter to the syringes.
c. Forcing air out of the connectors by slowly dispensing substance until it starts to protrude from the connector.
d. Using the connectors to join the syringes tip-to-tip.
e. Pushing the peptide solution to extrude through the orifice into the payload syringe, and continuing to push the peptide solution until the syringe is empty.
f. Pushing the mixed solution back through the orifice until all of the solution is in the peptide syringe.
g. Pushing the mixed solution through the orifice again.

In some embodiments, a reset peptide solution may be mixed with payload agents within about 1 minute to about 8 hours after the resetting process. In some embodiments, a reset peptide solution is mixed with payload agents within about 1, 2, 3, 4, 5, 6, 7, 8, 9, 10, 15, 20, 25, 30, 45, or 60 minutes, or within about 2, 3, 4, 5, 6, 7, 8, 9, 10, 11, 12, or 24 hours after the resetting process.

Applications

In some embodiments, a combination composition described herein is used to treat a disease or disorder, e.g., a disease or disorder known to be or suspected to be treated by a therapeutic agent described herein (e.g., infection, cancer, cardiovascular disease, neurological disease), and/or used in wound-healing, bone/cartilage repair/regeneration, soft tissue regeneration. A combination composition described herein can be administered to a subject in a variety of ways, and administration is not limited to any particular method. In some embodiments, a combination composition described herein is administered to a subject by, or is applied to, a device, medical device, implant, dental implant, breast implant, prosthesis, needle, stent, or catheter. Additional methods of administration are described in, e.g., Patent Application Nos. US2011/0002880; WO/2008/073395; US2011/0201541; US 2014/0329914; US 2015/0105336; WO/2014/136081; WO/2014/141143, and U.S. Pat. No. 7,846,891.

In some embodiments, an agent is or comprises a cellular lysate, e.g., a tumor lysate. In some such embodiments, a combination composition can treat or prevent cancer. In some embodiments, a tumor is or comprises a hematologic malignancy, including but not limited to, acute lymphoblastic leukemia, acute myeloid leukemia, chronic lymphocytic leukemia, chronic myelogenous leukemia, hairy cell leukemia, AIDS-related lymphoma, Hodgkin lymphoma, non-Hodgkin lymphoma, Langerhans cell histiocytosis, multiple myeloma, or myeloproliferative neoplasms. In some embodiments, a tumor is or comprises a solid tumor, including but not limited to breast carcinoma, a squamous cell carcinoma, a colon cancer, a head and neck cancer, ovarian cancer, a lung cancer, mesothelioma, a genitourinary cancer, a rectal cancer, a gastric cancer, or an esophageal cancer.

In some embodiments, an agent is or comprises a cell and/or tissue, e.g., a graft. In some such embodiments, a combination composition can be used, e.g., in wound healing. In some embodiments, an agent is or comprises a skin graft, e.g., a micrograft, e.g., a microscopic skin tissue column (see, e.g., Tam et al., Plast. Reconstr. Surg. Glob. Open 2013 Sep. 1(6): e47). In some embodiments, mixed thickness skin micrografts, split-thickness skin grafts, or full thickness skin grafts, including autologous grafts, are harvested and/or prepared, e.g., "minced", using any device or protocol, e.g., using an XPANSION® device or an XPANSION MICROGRAFTING SYSTEM® (SteadMed Medical, Fort Worth, Tex.). See also Hadjiiski, THE METHOD OF MICROGRAFTING IN THE TREATMENT OF LARGE AREA FULL-THICKNESS BURNS, Annals of Burns and Fire Disasters, vol. XIII, n. 3, September 2000.

In some embodiments, a combination composition described herein exhibits sustained or controlled release of a therapeutic agent. For example, upon administration to a subject, a therapeutic agent is released from the combination composition at a controlled rate such that a therapeutically effective amount of the therapeutic agent are maintained in the subject (e.g., locally and/or systemically) over an extended period of time, e.g., from about 12 hours to 24 hours, 36 hours, 48 hours, 3 days, 4, days, 5, days, 6, days, 7 days, or longer. See, e.g., Nishimura et al., Eur. J. Pharm Sci. 45:1-7 (2012); Liu et al., Int. J. Nanomedicine 6:2143-53 (2011); Gelain et al., J. Control Release 145:231-9 (2010).

EXEMPLIFICATION

Example 1: Mixing a Stored/Aged Peptide Solution with a Payload

The present Example reveals source of problem that sometimes stored/aged peptide solutions may not distribute payload agents homogeneously. Fresh RADA16 (SEQ ID NO:1) solution was prepared by dissolving dried RADA16 (SEQ ID NO:1) in water, filtering through a sterile filter (0.22 μm), and then aseptically filling into sterile syringes, at a peptide concentration of 2.5% (w/v) (provided by 3-D Matrix). A 1% Congo Red (Sigma-Aldrich C6277) solution was prepared. Various mixing methods for 2.5% RADA16 (SEQ ID NO:1) solution and 1 w/v % Congo Red solution were explored to achieve homogeneous mixing.

First, a mixing barrel system with dual syringes as shown in FIG. 3A was used. However, the phase of mixture was not homogeneous as shown in FIG. 3B. The apparent viscosity of the mixture was still high.

Next, a luer lock connector system with two syringes was used as shown in FIG. 3C. 2.5% RADA16 (SEQ ID NO:1) solution was placed in one syringe and 1% Congo Red solution was filled in the other syringe and the both plungers were moved back and forth 15 times. However, the mixture was not homogeneous as shown in FIG. 3D. The apparent viscosity of the mixture was still high.

Common methods did not lead to mixing the stored/aged peptide solution and payloads agents homogeneously. However, when a pre-injection of 2.5% RADA16 (SEQ ID NO:1) solution through a needle was added before using the luer lock connector system with two syringes, the combination composition mixed homogeneously. This method is shown in FIG. 4.

Example 2: Resetting and Mixing a Peptide Solution with Needles

The present Example describes, among other things, an exemplary preparation of homogeneous peptide solution/combination composition using needles. The needle gauge effects on homogeneity of the mixed solutions were observed.

A 2.5% RADA16 (SEQ ID NO:1) solution and a 1 w/v % Congo Red solution were prepared. The RADA16 (SEQ ID NO:1) solution and the Congo Red solution were coarsely mixed by shuttling through 25 G (Inner Diameter (ID)=0.010"). Then, the coarse mixture was expressed through various needle sizes into a surface drop as shown in FIG. 5. The surface drops were disrupted with a 30 G needle by holding the needle horizontally and dragging the needle shaft through the surface bead. The drop from the 25 G needle appeared to have greater viscosity compared to drops from 30 G or 32 G needles, but all drops returned to their original shape.

The solutions were placed on slide glass and covered with cover glass. While FIG. 6A shows spots and striations, FIG. 6B does not show them and presents smooth color gradient with changing thickness of the solution.

The solutions were observed with optical microscope (TESA V300 DCC) with magnification of 27× (FIGS. 7A-7D) and 164× (FIGS. 8A-8D). The results with various needle gauges are summarized in Table 1. When 2.5% RADA16 (SEQ ID NO:1) solution was injected through 30 G and 32 G needles, the mixture was apparently and microscopically homogeneous.

TABLE 1

Mixing status with different needle gauge size.

| Used needle gauge | Apparent homogeneity | Microscopic homogeneity | Apparent viscosity | Injection difficulty |
|---|---|---|---|---|
| 25G | Not homogeneous | Not homogeneous | Viscose | Easy |
| 27G | Homogeneous | Not homogeneous | Medium | Medium |
| 30G | Homogeneous | Homogeneous | low | hard |
| 32G | Homogeneous | Homogeneous | low | Very hard |

The injection of the solution through a needle or a mesh may change the secondary structure of RADA16 (SEQ ID NO:1) molecules. Through the needle or mesh, the self-assembled peptide structure may change from three-dimensionally assembled beta-sheet structure to random structure due to the applied high shear stress. The dye molecules may be homogeneously mixed with the peptide molecules which bear random structure rather than three-dimensionally assembled beta-sheet structure. When the peptide solution was injected through a needle or mesh, its apparent viscosity became lower. Three-dimensionally assembled beta-sheet structure of the solution may be changed to a random structure.

Example 3: Resetting and Mixing a Peptide Solution with Meshes

The present Example describes, among other things, an exemplary preparation of homogeneous peptide solution/combination composition using meshes. The effect of mesh size on homogeneity of the mixed solutions was determined.

A 2.5% RADA16 (SEQ ID NO:1) solution and a 1 w/v % Congo Red solution were prepared. A standard syringe was used to draw up an aliquot of the peptide solution and then it was homogenized using meshes with various sizes of pore (e.g., 10, 25, 43, and 73 μm). Next, the syringe was connected to the syringe containing the Congo Red solution, and mixed back and forth 6 times.

Figures 10A, 10B:
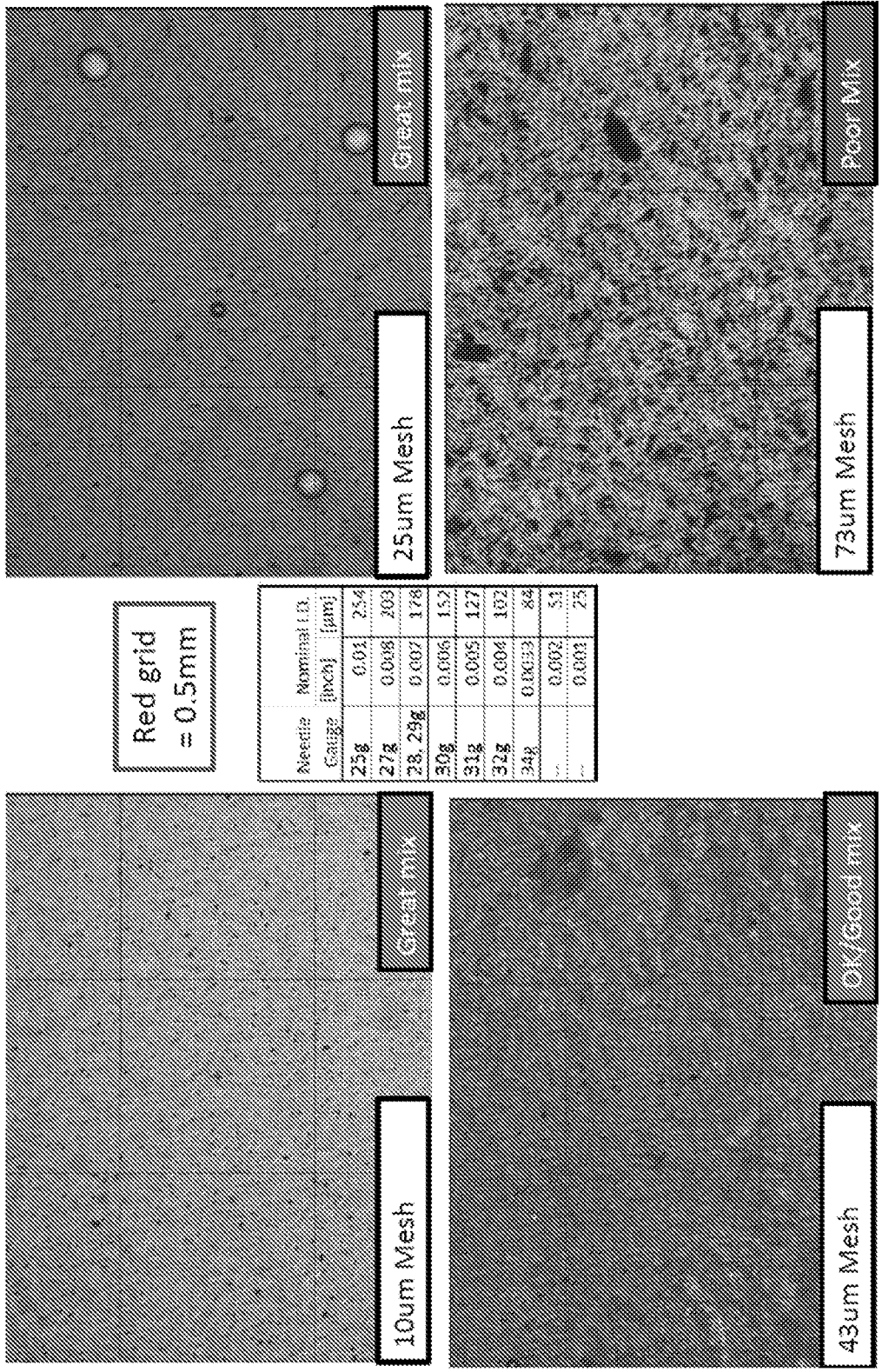
FIGS. 10A and 10B are optical microscopy images of the solutions treated with various sizes of meshes. The magnification is 164×.
Figure 11:
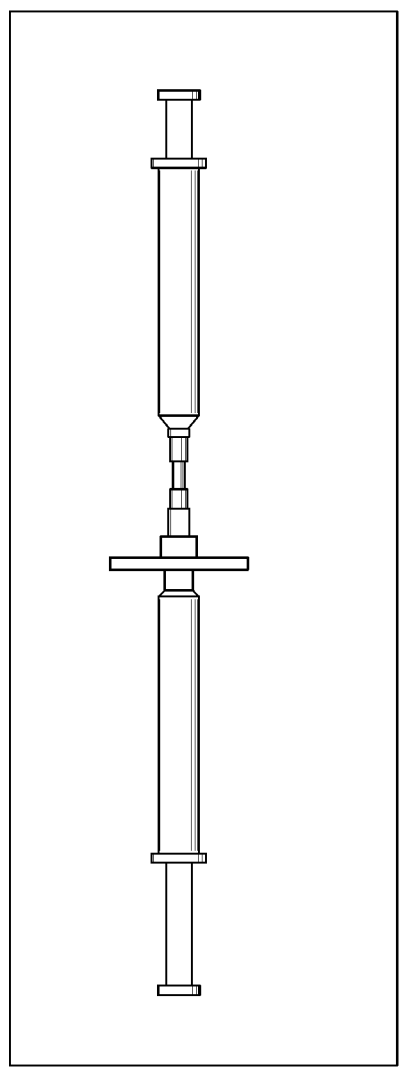
FIG. 11 shows a mixing system set up to measure Storage modulus of various solutions.

The solutions were observed with optical microscope (TESA V300 DCC) with magnification of 27× (FIGS. 9A-9D) and 164× (FIGS. 10A and 10B). The results with various mesh sizes are summarized in Table 2. When 2.5% RADA16 (SEQ ID NO:1) solution was injected through meshes with 10 or 25 μm pore, the mixture was apparently and microscopically homogeneous.

TABLE 2

Mixing status with homogenization of 2.5% RADA16 (SEQ ID NO: 1) solution through meshes with different pore size.

| Mesh size (μm) | Apparent homogeneity | Microscopic homogeneity | Apparent viscosity |
|---|---|---|---|
| 10 | Homogeneous | Homogeneous | Low |
| 25 | Homogeneous | Homogeneous | Low |
| 43 | Homogeneous | Not homogeneous | Medium |
| 73 | Not homogeneous | Not homogeneous | Viscose |

In some embodiments, a mesh may require lower force than a needle to homogenize a peptide solution. Multiple orifices in parallel gives homogeneous mix with less force required as orifice count increases. For example, wire mesh assemblies (e.g., available off-the-shelf) could emulate a massively-parallel orifice array. However, a mesh has round hole edges, likely resulting in reduced shear than sharp-edged orifices (e.g., needle). Hole sizes of a mesh may not be inconsistent. In some embodiments, a mesh may be harder to achieve part-to-part repeatability due to the inconsistent hole sizes. The present Example shows successful application of a mesh for a homogenizing a peptide solution despite the challenges.

Example 4: Rheological Properties

The present Example describes, among other things, rheological properties of various peptide compositions prepared and treated differently.

A 2.5% RADA16 (SEQ ID NO:1) solution was prepared. The syringe-aged solution in this Example was stored at 4° C. for 2 days. For homogenizing the RADA16 (SEQ ID NO:1) solutions, the solutions were 15 times passed through a mesh unit with 0.2 μm pore size.

Storage modulus was measured for four samples as shown in Table 3. The measurements were performed on peptide solutions using a rheometer (DHR-1, TA Instruments) at 0.1 Pa of stress and 5 rad/sec of frequency using a 20 mm plate. Storage modulus was measured three times for each sample, and the data are shown as Average±Standard Deviation.

TABLE 3

Storage modulus measurement for solutions with various status/treatment

| Sample No. | Fresh or aged | Homogenization | Storage Modulus G' (Pa) |
|---|---|---|---|
| 1 | Fresh | No treatment | 5.1 ± 1.9 |
| 2 | Fresh | Mesh treatment | 1.7 ± 0.2* |
| 3 | Aged | No treatment | 400 ± 9.1 |
| 4 | Aged | Mesh treatment | 17.7 ± 4.9* |

*noted when the values are significantly different compared to the values of untreated samples.

As shown in Table 3, sample No. 1 (Fresh, no treatment) has relatively low storage modulus. Sample No. 3 shows 80 to 400 times increased storage modulus compared to fresh solutions. Sample No. 4, which prepared from Sample No. 3 exhibits significantly low storage modulus than Sample No. 3.

The rheological measurements show that a homogenization treatment on a stored RADA16 (SEQ ID NO:1) solution created a new composition with a certain storage modulus that allows for both the RADA16 (SEQ ID NO:1) to be properly mixed with the desired payloads as well as to maintain a high enough viscosity for optimal gelation of RADA16 (SEQ ID NO:1).

Example 5: Pressure Measurement

The present Example describes, among other things, required force and pressure for homogenizing a peptide solution.

Figure 12:
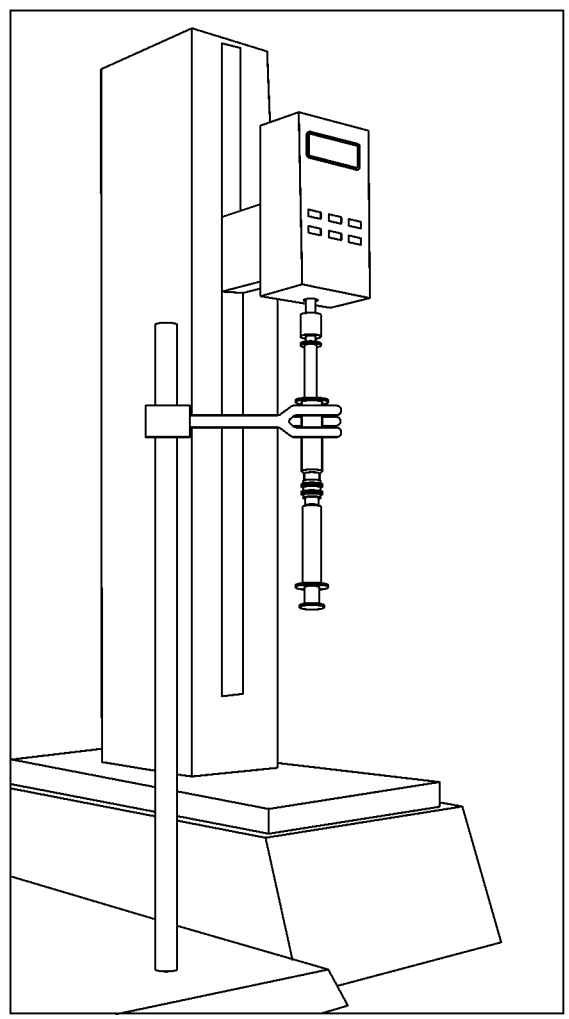
FIG. 12 shows an experimental set up to measure applied force on peptide solutions/combination compositions.

Required pressure to force a RADA16 (SEQ ID NO:1) 2.5% solution through a needle or a mesh was calculated by measuring the force on a syringe plunger. The syringe was secured in a heavy-duty ring stand along the axis of motion of the force measurement test stand as shown in FIG. 12. For needle experiments, the plunger of a 1 mL syringe with 0.185" ID was depressed at rate of 1060 mm/min, creating a flow rate of 0.33 mL/sec. For mesh experiments, the plunger of a 3 mL syringe with 0.386" ID was depressed at rate of 1060 mm/min, creating a flow rate of 1.33 mL/sec.

Table 4 shows the force testing results and calculated pressure for needle experiments. Results shown are an average of three runs.

TABLE 4

Force measurement and pressure calculation for solutions treated with various needle sizes

| Needle ID (in) | Measured Force (lbf) | Pressure (PSI) |
|---|---|---|
| 0.003 | 18.3 | 680.8 |
| 0.004 | 9.68 | 360.1 |

TABLE 4-continued

Force measurement and pressure calculation for
solutions treated with various needle sizes

| Needle ID (in) | Measured Force (lbf) | Pressure (PSI) |
|---|---|---|
| 0.005 | 4.33 | 160.9 |
| 0.006 | 2.62 | 97.3 |

Figure 13B:
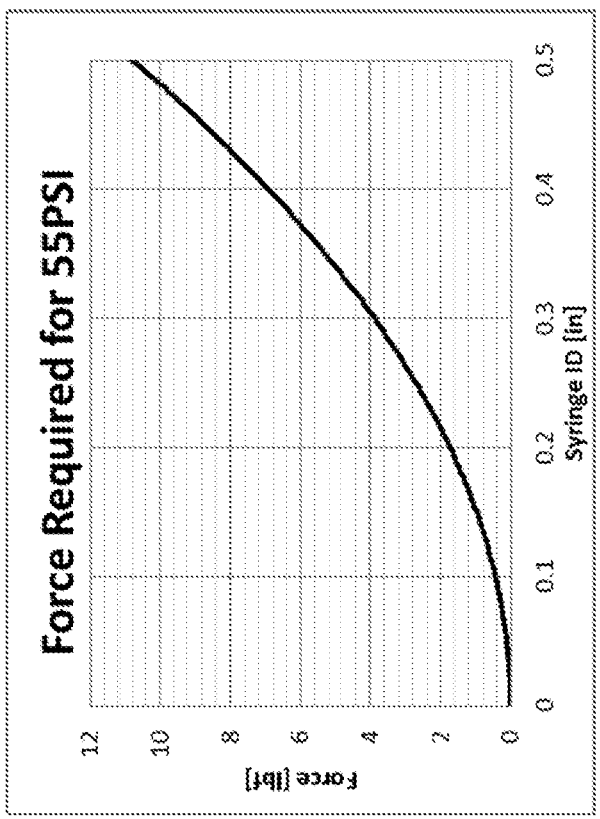
FIG. 13B is a graph showing required force as a function of syringe inner diameter in order to apply 55 PSI to a peptide solution at a flow rate of 1.33 mL/sec. Shear stress was applied using a mesh.
Figure 13A:
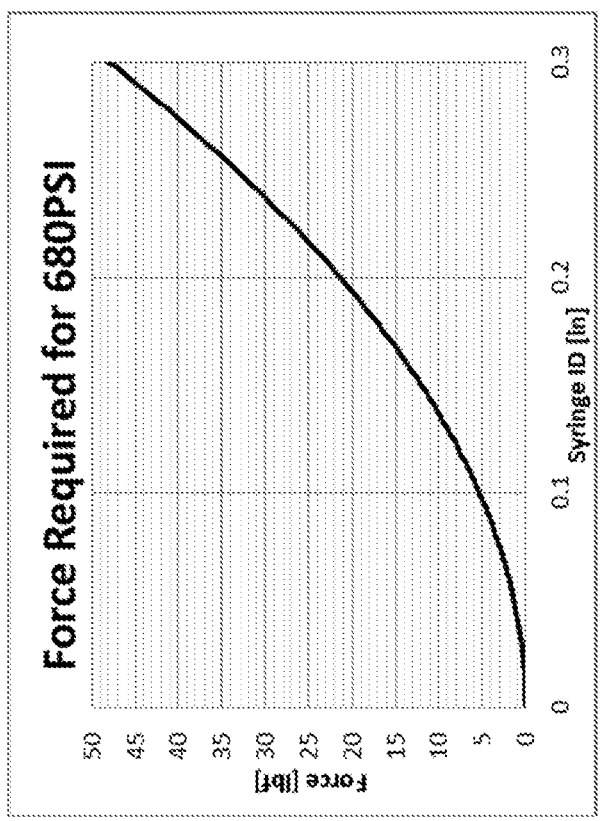
FIG. 13A is a graph showing required force as a function of syringe inner diameter in order to apply 680 PSI to a peptide solution at a flow rate of 0.33 mL/sec. Shear stress was applied using a needle.

FIG. 13A illustrates the required force as a function of the syringe size to apply 680 PSI (e.g., to extrude the RADA16 (SEQ ID NO:1) 2.5% solution through a 0.003" needle at 0.33 ml/sec) to a peptide solution. As flow rate is proportional to pressure, pressure required to generate other flow rates can be easily determined. Doubling the pressure creates double the flow (assuming the geometry and viscosity are constant.)

Table 5 shows the force testing results and calculated pressure for mesh experiments. Results shown are an average of three runs. FIG. 13B illustrates the required force as a function of the syringe size to apply 55 PSI (e.g., to extrude the RADA16 (SEQ ID NO:1) 2.5% solution through a 25 µm mesh at 1.33 ml/sec) to a peptide solution. Flow rate is proportional to pressure, so pressures required to generate other flow rates can be easily determined. Doubling the pressure creates double the flow (assuming the geometry and viscosity are constant.)

TABLE 5

Force measurement and pressure calculation
for solutions treated with a mesh

| Mesh (in) | Measured Force (lbf) | Pressure (PSI) |
|---|---|---|
| 25 | 6.4 | 54.7 |

Table 5 shows the force testing results and calculated pressure for needle experiments. Results shown are an average of three runs.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of manufacturing a liquid combination composition comprising a self-assembling peptide and a therapeutic agent, the method comprising steps of:
    before or after combining the therapeutic agent with a liquid preparation of the self-assembling peptide, homogenizing the liquid preparation by subjecting it to high shear stress sufficient to reduce its initial storage modulus by at least a factor of three;
    wherein the self-assembling peptide comprises from about 7 to about 32 alternating hydrophobic and hydrophilic amino acids.

2. The method of claim 1, wherein the initial storage modulus is about 100 Pa to about 3000 Pa at 5 rad/sec of frequency and 0.1 Pa of oscillation stress.

3. The method of claim 2, wherein the step of homogenizing comprises subjecting to high shear stress sufficient to reduce the initial storage modulus by at least 80-400 fold.

4. The method of claim 2, wherein the step of homogenizing comprises subjecting the liquid preparation to high shear stress by passing it through at least one shear-thinning unit.

5. The method of claim 4, wherein the at least one shear-thinning unit is or comprises at least one needle.

6. The method of claim 5, wherein the at least one needle is at least 1 mm long.

7. The method of claim 5, wherein the at least one needle has a gauge greater than about 27.

8. The method of claim 4, wherein the at least one shear-thinning unit is or comprises at least one screen with micro- or nano-sized holes.

9. The method of claim 8, wherein the micro- or nano-sized holes have a largest dimension smaller than about 43 μm.

10. The method of claim 8, wherein the screen is made at least in part of a material selected from the group consisting of stainless-steel, tungsten, titanium, silicon, ceramic, plastic, and combinations thereof.

11. The method of claim 8, wherein thickness of the screen is about 10 μm to about 10 mm.

12. The method of claim 1, wherein the high shear stress is within a range of about 30 to about 200 Pa.

13. The method of claim 1, wherein the self-assembling peptide has an amino acid sequence selected from the group consisting of RADA16 as set forth in SEQ ID NO:1, IEIK13 as set forth in SEQ ID NO:3, and KLD12 as set forth in SEQ ID NO:2.

14. The method of claim 13, wherein the self-assembling peptide is present at a concentration of at least 2.5% weight to volume.

15. A combination composition prepared using the method of claim 1.

16. The method of claim 8, wherein the micro- or nano-sized holes have a largest dimension of about 25 μm or less.

17. The method of claim 1, wherein, prior to the step of homogenizing, the liquid preparation of the self-assembling peptide had been stored for a period of at least 2 days.

18. A method comprising steps of:
    combining a liquid preparation comprising at least 1% weight/volume of a self-assembling peptide having an amino acid sequence selected from the group consisting of RADA16 as set forth in SEQ ID NO:1, IEIK13 as set forth in SEQ ID NO:3, and KLD12 as set forth in SEQ ID NO:2 with a therapeutic agent so that a combination liquid composition is created; and
    before or after the step of combining, treating the liquid preparation by subjecting it to high shear stress sufficient to reduce its initial storage modulus by at least a factor of three.

19. The method of claim 18, wherein, prior to the step of treating, the liquid preparation had been stored for a period of at least 2 days.

20. The method of claim 18 or claim 19, wherein the liquid preparation comprises at least 2.5% by weight/volume of the self-assembling peptide.

21. The method of claim 18, wherein, after the step of treating, the combination liquid composition is characterized by microscopic homogeneity.

22. The method of claim 2, wherein the step of homogenizing comprises subjecting to high shear stress by one or more syringes.

23. The method of claim 18 or 19, wherein the step of subjecting to high shear stress comprises passing the liquid preparation through at least one shear-thinning unit selected from the group consisting of needles, membranes, screens, and combinations thereof.

24. The method of claim 18 or 19, wherein the step of subjecting to high shear stress comprises at least one step of passing from a first syringe, through a chamber with pores, into a second syringe.

25. The method of claim 24, wherein the pores have a size pore size of about 0.45 μm to 200 μm.

26. The method of claim 25, wherein the pore size is about 1 μm to 150 μm.

27. The method of claim 25, wherein the pore size is about 1 μm to 100 μm.

28. The method of claim 25, wherein the pore size is about 5 μm to 50 μm.

29. The method of claim 24, wherein the step of passing from a first syringe, through a chamber with pores, into a second syringe comprises steps of:

providing the liquid preparation loaded into the first syringe;

pushing the liquid preparation out of the first syringe, through a connector that is or comprises the chamber with pores, and into the second syringe, loaded with the therapeutic agent so that the liquid preparation and therapeutic agent are mixed;

pushing the mixture back through the connector into the first syringe;

optionally further pushing the mixture back and/or forth through the connector between the first and second syringes.

\* \* \* \* \*